(12) United States Patent
Blazej et al.

(10) Patent No.: US 9,080,162 B2
(45) Date of Patent: Jul. 14, 2015

(54) CELLULASE VARIANTS

(75) Inventors: Robert Blazej, San Francisco, CA (US); Nicholas Toriello, Woodside, CA (US); Charles Emrich, San Francisco, CA (US); Richard N. Cohen, Oakland, CA (US); Nitzan Koppel, Sunnyvale, CA (US)

(73) Assignee: Novozymes, A/S, Bagsvaerd (DK)

( * ) Notice: Subject to any disclaimer, the term of this patent is extended or adjusted under 35 U.S.C. 154(b) by 77 days.

(21) Appl. No.: 14/111,321

(22) PCT Filed: Apr. 11, 2012

(86) PCT No.: PCT/US2012/033138
§ 371 (c)(1),
(2), (4) Date: Dec. 18, 2013

(87) PCT Pub. No.: WO2012/142171
PCT Pub. Date: Oct. 18, 2012

(65) Prior Publication Data
US 2014/0113335 A1      Apr. 24, 2014

Related U.S. Application Data

(60) Provisional application No. 61/474,633, filed on Apr. 12, 2011.

(51) Int. Cl.
*C12P 19/14* (2006.01)
*C12P 7/10* (2006.01)
*C12N 9/42* (2006.01)

(52) U.S. Cl.
CPC ..................................... *C12N 9/2437* (2013.01)

(58) Field of Classification Search
CPC combination set(s) only.
See application file for complete search history.

(56) References Cited

PUBLICATIONS

Zhou et al, 2004, Biochemistry 43, 9655-9663.
Li et al, 2010, Appl Environ Microbiol 76(8)-2582-2588.
Li et al, 2007, Appl Environ Microbiol 73(10)-3165-3172.
Eecovar-Kousen JM et al, 2004, Appl Biochem Biotechnol 287-297.

*Primary Examiner* — Kagnew H Gebreyesus
(74) *Attorney, Agent, or Firm* — Eric J. Fechter

(57) ABSTRACT

This invention provides novel variant cellulolytic enzymes having improved activity and/or stability. In certain embodiments the variant cellulotyic enzymes comprise a glycoside hydrolase with or comprising a substitution at one or more positions corresponding to one or more of residues F64, A226, and/or E246 in *Thermobifida fusca* Cel9A enzyme. In certain embodiments the glycoside hydrolase is a variant of a family 9 glycoside hydrolase. In certain embodiments the glycoside hydrolase is a variant of a theme B family 9 glycoside hydrolase.

58 Claims, 11 Drawing Sheets

**Amino acid sequence of novel *Thermobifida fusca* Cel9A variant ("F1")**

EPAFNYAEALQKSMFFYEAQRSGKLPENNRVSWRGDSGLNDGADVGLDLTGG
WYDAGDHVKFGIPMAFTATMLAWGAIESPEGYIRSGQMPYLKDNLRWVNDYF
IKAHPSPNVLYVQVGDGDADHKWWGPAEVMPMERPSFKVDPSCPGSDVAAET
AAAMAASSIVFADDDPAYAATLVQHAKQLYTFADTYRGVYSDCVPAGAFYNS
WSGYQDELVWGAYWLYKVTGDDSYLAKAEYEYDFLSTGQQTDLRSYRWTIAW
DDKSYGTYVLLAKETGKQKYIDDANRWLDYWTVGVNGQRVPYSPGGMAVLDT
WGALRYAANTAFVALVYAKVIDDPVRKQRYHDFAVRQINYALGDNPRNSSYV
VGFGNNPPRNPHHRTAHGSWTDSIASPAENRHVLYGALVGGPGSPNDAYTDD
RQDYVANEVATDYNAGFSSALAMLVEEYGGTPLADFPPTEEPDGPEIFVEAQ
INTPGTTFTEIKAMIRNQSGWPARMLDKGTFRYWFTLDEGVDPADITVSSAY
NQCATPEDVHHVSGDLYYVEIDCTGEKIFPGGQSEHRREVQFRIAGGPGWDP
SNDWSFQGIGNELAPAPYIVLYDDGVPVWGTAPEEGEEPGGGEGPGGGEEPG
EDVTPPSAPGSPAVRDVTSTSAVLTWSASSDTGGSGVAGYDVFLRAGTGQEQ
KVGSTTRTSFTLTGLEPDTTYIAAVVARDNAGNVSQRSTVSFTTLAENGGGP
DASCTVGYSTNDWDSGFTASIRITYHGTAPLSSWELSFTFPAGQQVTHGWNA
TWRQDGAAVTATPMSWNSSLAPGATVEVGFNGSWSGSNTPPTDFTLNGEPCA
LA

*Fig. 1A*

DNA sequence of F1

GAACCGGCATTCAACTACGCGGAAGCACTGCAAAAATCCATGTTCTTCTACGAAGCTCAAC
GCTCAGGTAAACTGCCGGAAAATAACCGTGTTTCGTGGCGCGGTGATAGCGGTCTGAACGA
TGGTGCAGACGTCGGCCTGGATCTGACCGGCGGTTGGTATGATGCCGGTGACCATGTGAAA
TTTGGCaTCCCGATGGCTTTCACCGCGACGATGCTGGCCTGGGGTGCAATTGAATCTCCGG
AAGGTTATATCCGCAGTGGCCAGATGCCGTACCTGAAAGATAACCTGCGTTGGGTGAATGA
CTATTTTATTAAAGCGCATCCGTCTCCGAATGTTCTGTACGTTCAAGTCGGTGACGGCGAT
GCCGACCACAAATGGTGGGGTCCGGCAGAAGTGATGCCGATGGAACGCCCGAGTTTCAAAG
TCGATCCGTCGTGCCCGGGCAGCGACGTGGCAGCAGAAACCGCAGCTGCGATGGCCGCAAG
CTCTATCGTCTTTGCCGATGACGATCCGGCGTATGCGGCAACCCTGGTGCAGCACGCTAAA
CAACTGTACACCTTCGCGGACACGTATCGTGGTGTCTACTCTGATTGTGTGCCGGCTGGTG
CGTTTTATAACAGTTGGTCCGGCTACCAGGATGAACTGGTGTGGGGTGCTTATTGGCTGTA
CAAAGtGACCGGCGACGATAGCTATCTGGCCAAAGCAGAATATGAATACGATTTTCTGAGC
ACCGgACAGCAAACGGATCTGCGTAGCTACCGCTGGACCATTGCGTGGGACGATAAAAGCT
ATGGCACCTATGTGCTGCTGGCCAAAGAAACGGGCAAACAGAAATATATCGACGATGCAAA
CCGCTGGCTGGATTACTGGACCGTGGGTGTTAATGGCCAACGTGTTCCGTATAGCCCGGGC
GGTATGGCCGTCCTGGATACCTGGGGTGCACTGCGCTATGCCGCAAATACGGCTTTCGTGG
CGCTGGTTTACGCCAAAGTTATTGACGATCCGGTCCGTAAACAGCGCTATCATGATTTTGC
TGTGCGCCAAATCAACTACGCGCTGGGTGATAACCCGCGTAATAGTTCCTATGTGGTTGGT
TTCGGCAACAATCCGCCGCGTAATCCGCATCACCGTACCGCGCATGGCTCGTGGACGGATA
GCATTGCCTCTCCGGCAGAAAACCGCCACGTCCTGTATGGTGCACTGGTGGGCGGTCCGGG
CTCCCCGAATGACGCGTATACCGACGATCGTCAGGATTACGTGGCCAACGAAGTTGCAACG
GATTATAATGCCGGCTTTTCATCGGCTCTGGCGATGCTGGTTGAAGAATACGGTGGCACCC
CGCTGGCAGACTTTCCGCCGACGGAAGAACCGGATGGTCCGGAAATTTTCGTTGAAGCGCA
GATCAACACCCCGGGCACCACGTTTACGGAAATTAAAGCTATGATCCGTAATCAAAGCGGT
TGGCCGGCGCGCATGCTGGACAAAGGCACCTTTCGTTATTGGTTCACGCTGGATGAAGGTG
TTGATCCGGCGGACATTACCGTTAGCTCTGCTTACAACCAGTGCGCGACGCCGGAAGATGT
CCATCACGTGTCCGGTGACCTGTATTACGTGGAAATTGATTGTACCGGCGAAAAAATCTTC
CCGGGCGGTCAATCAGAACATCGTCGCGAAGTTCAATTTCGTATCGCCGGCGGTCCGGGTT
GGGACCCGTCTAACGACTGGAGTTTTCAGGGTATTGGCAATGAACTGGCCCCGGCACCGTA
TATCGTGCTGTACGACGATGGTGTCCCGGTGTGGGGCACCGCACCGGAAGAAGGCGAAGAA
CCGGGCGGTGGCGAAGGTCCGGGTGGCGGTGAAGAACCGGGCGAAGATGTCACCCCGCCGT
CCGCACCGGGCTCACCGGCAGTTCGTGATGTCACCTCAACGTCGGCCGTTCTaACCTGGTC
CGCAAGTTCCGACACGGGCGGTTCAGGCGTGGCTGGCTATGATGTTTTCCTGCGCGCGGGC
ACCGGCCAGGAACAAAAAGTGGGTTCTACCACGCGTACGAGTTTTACCCTGACGGGCCTGG
AACCGGATACCACGTATATTGCTGCGGTCGTGGCTCGCGATAACGCGGGTAATGTTAGTCA
GCGTTCCACCGTCTCATTCACCACGCTGGCAGAAAACGGCGGTGGCCCGGATGCATCGTGC
ACCGTTGGTTATAGCACGAATGATTGGGACTCCGGCTTTACCGCCTCAATTCGCATCACCT
ATCATGGCACCGCACCGCTGTCATCGTGGGAACTGAGTTTTACCTTCCCGGCTGGTCAGCA
AGTGACCCACGGCTGGAATGCCACGTGGCGTCAGGATGGTGCCGCAGTTACCGCGACGCCG
ATGTCTTGGAACAGCTCTCTGGCTCCGGGTGCAACCGTTGAAGTCGGTTTTAATGGCAGTT
GGAGTGGTAGCAACACCCCGCCGACCGATTTCACCCTGAATGGCGAACCGTGCGCTCTGGC
A

*Fig. 1B*

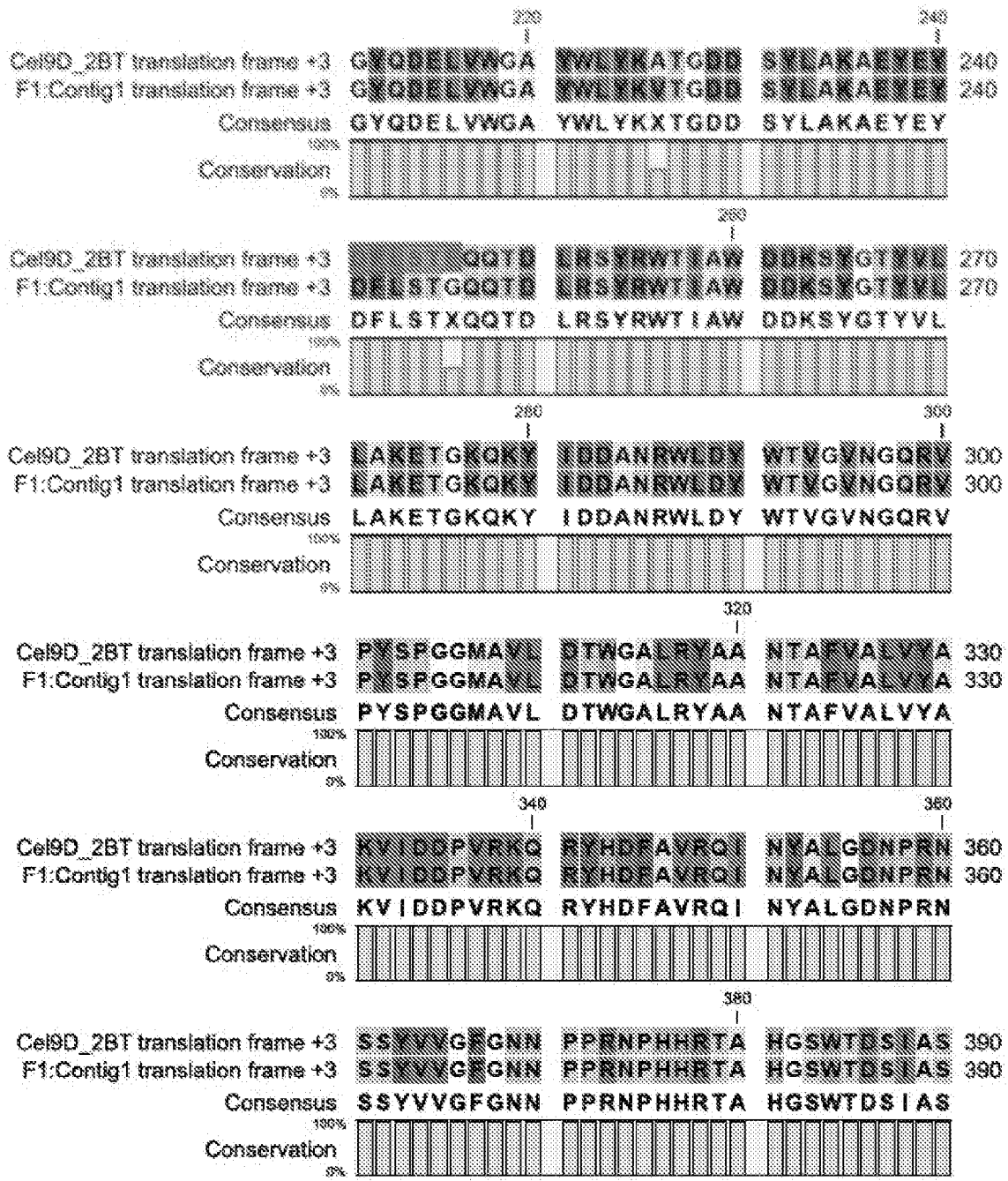
*Fig. 2, cont'd.*

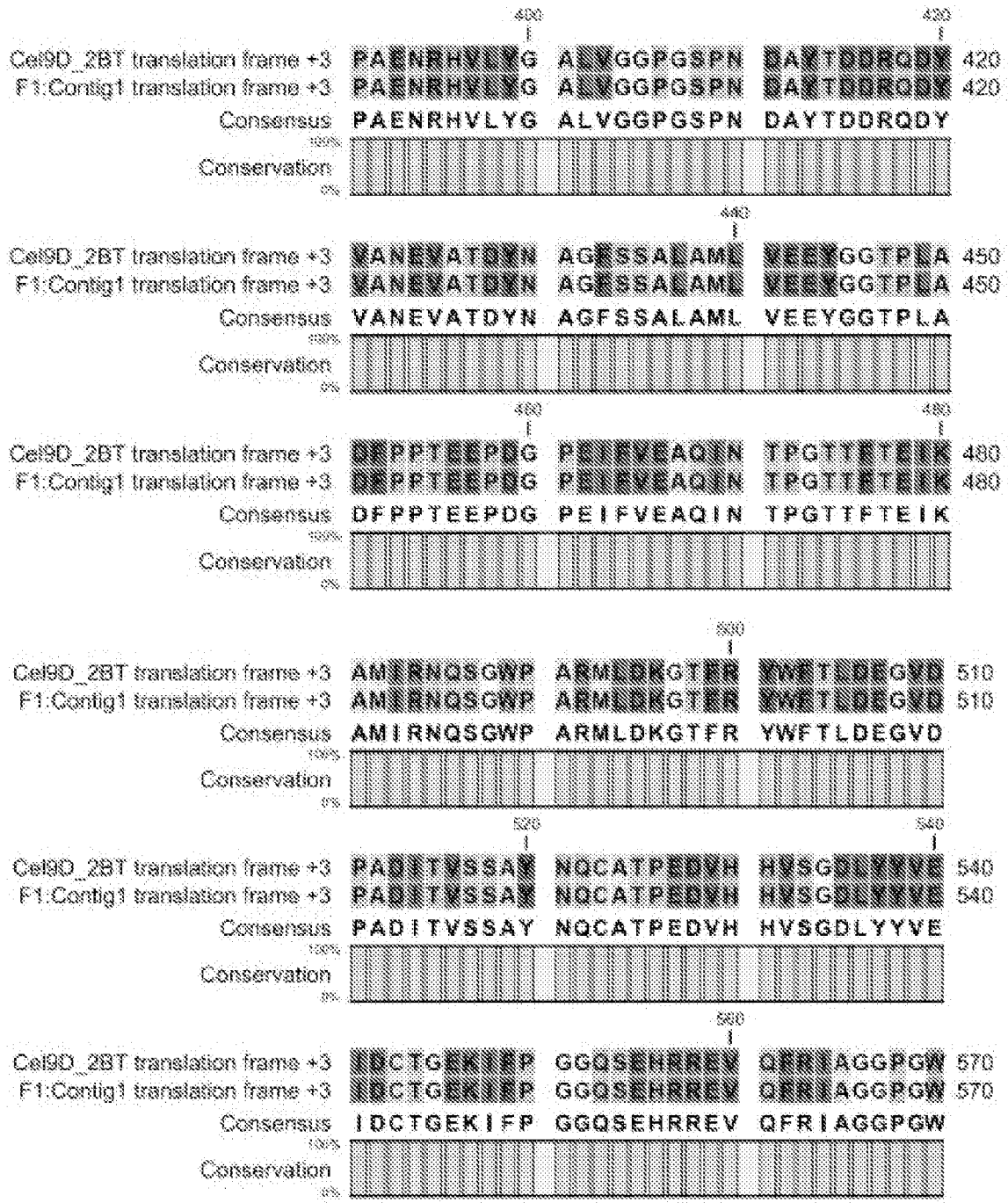
Fig. 2, cont'd.

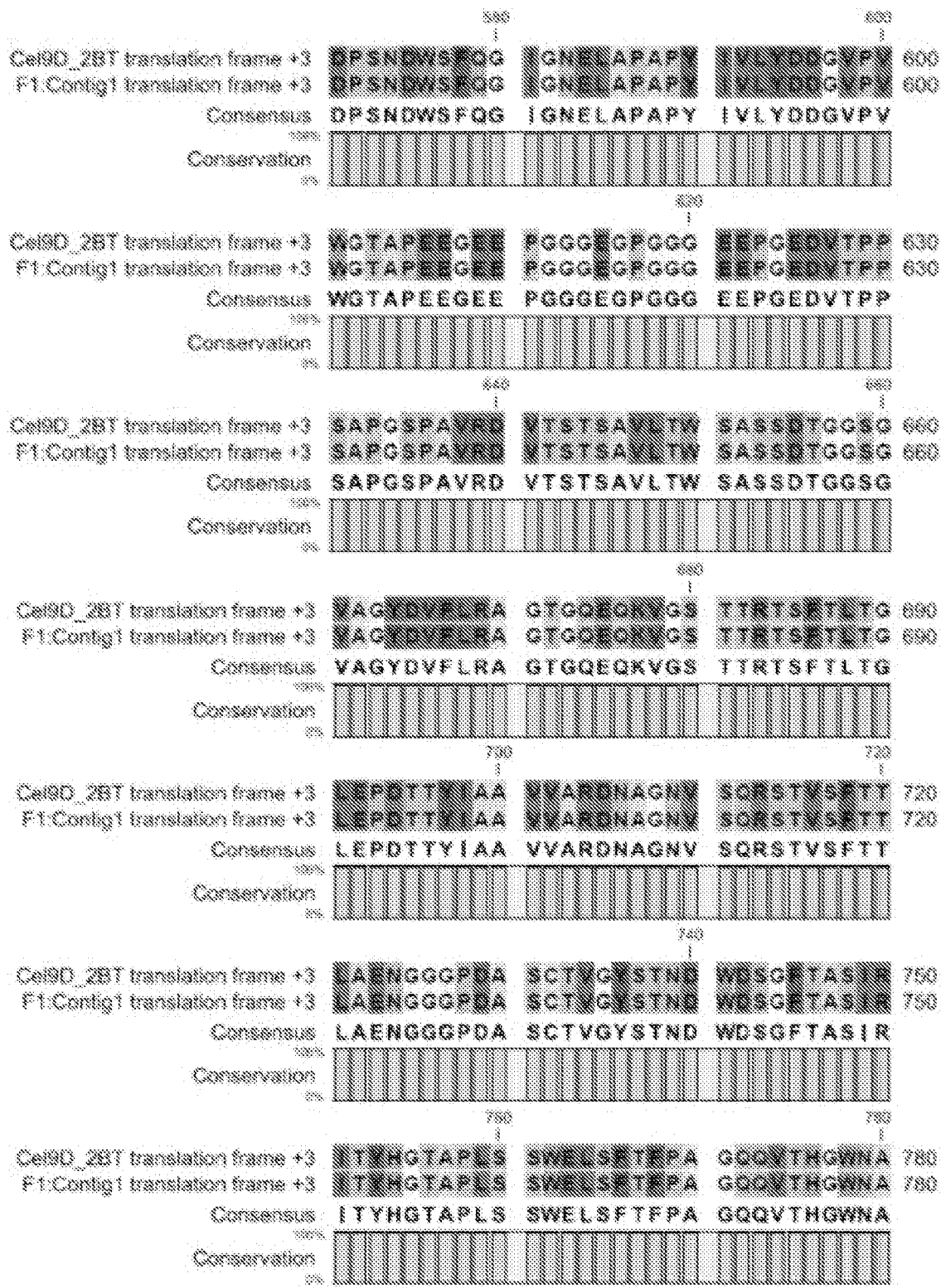
Fig. 2, cont'd.

```
Cel9D_2BT translation frame +3   TWRQDGAAVT  ATPMSWNSSL  APGATVEVGF  810
F1:Contig1 translation frame +3  TWRQDGAAVT  ATPMSWNSSL  APGATVEVGF  810
                      Consensus  TWRQDGAAVT  ATPMSWNSSL  APGATVEVGF
                   Conservation Cel9D_2BT translation frame +3   NGSWSGSNTP  PTDFTLNGEP  CALA**      836
F1:Contig1 translation frame +3  NGSWSGSNTP  PTDFTLNGEP  CALA**      836
                      Consensus  NGSWSGSNTP  PTDFTLNGEP  CALAXX
                   Conservation
```

*Fig. 2, cont'd.*

*Alignment between wild-type Thermobifida fusca Cel9A and Clostridium phytofermentans Cphy3367 and structures showing 3D similarity*

Score = 612 bits (1577), Expect = 4e-179, Method: Compositional matrix adjust.

Identities = 318/618 (52%), Positives = 407/618 (66%), Gaps = 22/618 (3%)

Query = *Thermobifida fusca* Cel9A, Sbjct = *Clostridium phytofermentans* Cphy3367

```
Query    1   ETNYNYGEALQKSIMFYEFQRSGKLPSTIRNNWRGDSGLTDGADVGLDLTGGWYDAGDHV   60
             E +NY EALQKS+ FYE QRSGKLP  R +WRGDSGL DGADVGLDLTGGWYDAGDHV
Sbjct    1   EPAFNYAEALQKSMFFYEAQRSGKLPENNRVSWRGDSGLNDGADVGLDLTGGWYDAGDHV   60

Query   61   KFNLPLAYTVTMLAWAVYEEEATLSKAGQLSYLLDEIKWSSDYLIKCHPQANVFYYQVGN   120
             KF  P+A+T TMLAW   E       ++GQ+ YL D ++W +DY IK HP  NV Y QVG+
Sbjct   61   KFGFPMAFTATMLAWGAIESPEGYIRSGQMPYLKDNLRWVNDYFIKAHPSPNVLYVQVGD   120

Query  121   GNTDHSWWGPAEVMQMARPSYKVDLNNPGSTVVGEAAAALAATALIYKTKDPTYSATCLR   180
             G+ DH WWGPAEVM M RPS+KVD + PGS V  E AAA+AA+++++    DP Y+AT ++
Sbjct  121   GDADHKWWGPAEVMPMERPSFKVDPSCPGSDVAAETAAAMAASSIVFADDDPAYAATLVQ   180

Query  181   HAKELFNFADTTK---SDAGYTAASGFYTSYSGFYDELSWAATWIYLASGEATYLDKAES   237
             HAK+L+ FADT +   SD    A   FY S+SG+ DEL W A W+Y A+G+ +YL KAE
Sbjct  181   HAKQLYTFADTYRGVYSDC--VPAGAFYNSWSGYQDELVWGAYWLYKATGDDSYLAKAEY   238

Query  238   YVAKWGTEPQSSTLSYKWAQNWDDVHYGAALLLARITNKAIYKNNIEMHLDYWTTGYNGS   297
                  TE Q+    SY+W   WDD   YG +LLA+ T K  Y ++      LDYWT G NG
Sbjct  239   EYDFLSTEQQTDLRSYRWTIAWDDKSYGTYVLLAKETGKQKYIDDANRWLDYWTVGVNGQ   298

Query  298   RITYTPKGLAWLDSWGALRYATTTAFLASVYADWSGCSAGKVSTYNAFAKQQVDYALGST   357
             R+ Y+P G+A LD+WGALRYA   TAF+A VYA        K   Y+ FA +Q++YALG
Sbjct  299   RVPYSPGGMAVLDTWGALRYAANTAFVALVYAKVIDDPVRK-QRYHDFAVRQINYALGDN   357

Query  358   GR--SFVVGYGVNSPTRPHHRTAHSSWADSQTEPNYHRHTIYGALVGGPGN-NDSYEDNI   414
             R   S+VVG+G N P  PHHRTAH SW DS   P  +RH +YGALVGGPG+ ND+Y D+
Sbjct  358   PRNSSYVVGFGNNPPRNPHHRTAHGSWTDSIASPAENRHVLYGALVGGPGSPNDAYTDDR   417

Query  415   NNYVNNEIACDYNAGFVGALAKVYKTYGGTPIANFKAIETVTNDELFIQAGINASGPSFI   474
              +YV NE+A DYNAGF  ALA + + YGGTP+A+F   E       E+F++A IN G +F
Sbjct  418   QDYVANEVATDYNAGFSSALAMLVEEYGGTPLADFPPTEEPDGPEIFVEAQINTPGTTFT   477

Query  475   EVKALVFNETGWPARVTDKLSFKYFIDISEYVAKGYTKNDFTVSTNYNNGATTSALLPWD   534
             E+KA++ N++GWPAR+ DK +F+Y+ + E    G   D TVS+ YN  AT       +
Sbjct  478   EIKAMIRNQSGWPARMLDKGTFRYWFTLDE----GVDPADITVSSAYNQCATPEDVH--H   531

Query  535   AANNIYYVNVDFSGTKIYPGGQSAYKKEVQFRIAGPQNVNIWDNSNDYSFTQIANVSSGN   594
             +  ++YYV +D +G KI+PGGQS   +++EVQFRIAG      WD SND+SF  I  N
Sbjct  532   VSGDLYYVEIDCTGEKIFPGGQSEHRREVQFRIAGGPG---WDPSNDWSFQGIGN----E   584

Query  595   TVKTTYIPLYDNGKLVFG   612
                  YI LYD+G  V+G
Sbjct  585   LAPAPYIVLYDDGVPVWG   602
```

*Fig. 4*

*Clostridium phytofermentans* Cphy3367
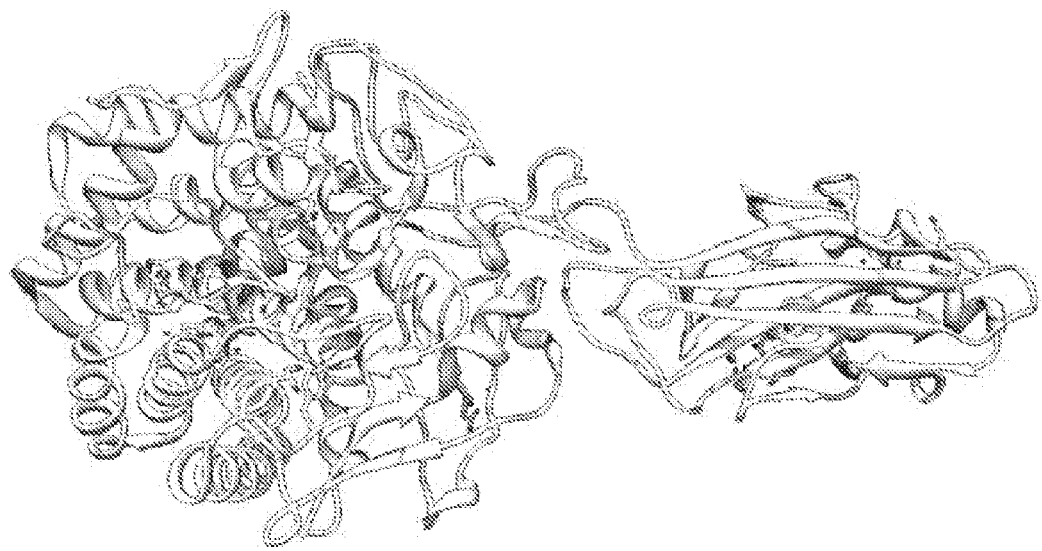
*Thermobifida fusca* Cel9A
*Fig. 5*

Additional examples of novel variants exhibiting increased cellulolytic activity "G03"
EPAFNYAEALQKSMFFYEAQRSGKLPENNRVSWRGDSGLNDGADVGLNLTGGWYDAGDHVK
FGFPMAFTATMLAWGAIESPEGYIRSGQMPYLKDNLRWVNDYFIKAHSSPNVLYVQVGDGD
ADHKWWGPAEVMPMERPSFKVDPSCPGSDVAAETAAAMAASSIVFADDDPAYAATLVQHAK
QLYTFADTYRGVYSDCVPASAFYNSWSGYQDELVWGAYWLYKATGDDSYLAKAEYEYDFLS
TEQQTDLRSYRWTIAWDDKSYGTYVLLAKETGKQKYIDDANRWLDYWTVGVNGQRVPYSPG
GMAVLDTWGALRYAANTAFVALVYAKVIDDPVRKQRYHDFAVRQINYALGDNPRNSSYVVG
FGNNPPRNPHHRTAHGSWTDSIASPAENRHVLYGALVGGPGSPNDAYTDDRQDYVANEVAT
DYNAGFSSALAMLVEEYGGTPLADFPPTEEPDGPEIFVEAQINTPGTTFTEIKAMIRNQSG
WPARMLDKGTFRYWFTLDEGVDPADITVSSAYNQCATPEDVHHVSGDLYYVEIDCTGEKIF
PGGQSEHRREVQFRIAGGPGWDPSNDWSFQGIGNELAPAPYIVLYDDGVPVWGTAPEEGEE
PGGGEGPGGGEEPGEDVTPPSAPGSPAVRDVTSTSAVLTWSASSDTGGSGVAGYDVFLRAG
TGQEQKVGSTTRTSFTLTGLEPDTTYIAAVVARDNAGNVSQRSTVSFTTLAENGGGPDASC
TVGYSTNDWDSGFTASIRITYHGTAPLSSWELSFTFPAGQQVTHGWNATWRQDGTAVTATP
MSWNSSLAPGATVEVGFNGSWSGSNTPPTDFTLNGEPCALA "G11"
EPAFNYAEALQKSMFFYEAQRSGKLPENNRVSWRGDSGLNDGADVGLDLTGGWYDAGDHVK
FGFPMAFTATMLAWGAIESPEGYIRSGQMPYLKDNLRWVNDYFIKAHPSPNVLYVQVGDGD
ADHKWWGPAEVMPMERPSFKVDPSCPGSDVAAETAAAMAASSIVFADDDPAYAATLVQHAK
QLYTFADTYRGVYSDCVPAGAFYNSWSGYQDELVWGAYWLYKATGDDSYLAKAEYEYDFLS
TEQQTDLRSYRWTIAWDDKSYGTYVLLAKETGKQKYIDDANRWLDYWTVGVNGQRVPYSPG
GMAVLDTWGALRYAANTAFVALVYAKVIDDPVRKQRYHDFAVRQINYALGDNPRNSSYVVG
FGNNPPRNPHHRTAHGSWTDSIASPAENRHVLYGALVGGPGSPNDAYTDDRQDYVANEVAT
DYNSGFSSALAMLVEEYGGTPLADFPPTEEPDGPEIFVEAQINTPGTTFTEIKAMIRNQSG
WPARMLDKGTFRYWFTLDEGVDPADITVSSAYNQCATPEDVHHVSGDLYYVEIDCTGEKIF
PGGQSEHRREVQFRIAGGPGWDPSNDWSFQGIGNELAPAPYIVLYNDGVPVWGTAPEEGEE
PGGGEGPGGGEEPGEDVTPPSAPGSPAVRDVTSTSAVLTWSASSDTGGSGVAGYDVFLRAG
TGQEQKVGSTTRTSFTLTGLEPDTTYIAAVVARDNAGNVSQRSTVSFTTLAENGGGPDASC
TVGYSTNDWDSGFTASIRFTYHGTASLSSWELSFTFPAGQQVTHGWNATWRQDGAAVTATP
MSWNSSLAPGATVEVGFNGSWSGSNTPPTDFTLNGEPCALA

*Fig. 6* ardalose (1,4-beta-D-glucan cel-

SEQUENCE LISTING

```
<160> NUMBER OF SEQ ID NOS: 9

<210> SEQ ID NO 1
<211> LENGTH: 834
<212> TYPE: PRT
<213> ORGANISM: Thermobifida fusca

<400> SEQUENCE: 1

Glu Pro Ala Phe Asn Tyr Ala Glu Ala Leu Gln Lys Ser Met Phe Phe
1               5                   10                  15

Tyr Glu Ala Gln Arg Ser Gly Lys Leu Pro Glu Asn Asn Arg Val Ser
            20                  25                  30

Trp Arg Gly Asp Ser Gly Leu Asn Asp Gly Ala Asp Val Gly Leu Asp
        35                  40                  45
```

```
Leu Thr Gly Gly Trp Tyr Asp Ala Gly Asp His Val Lys Phe Gly Ile
     50                  55                  60

Pro Met Ala Phe Thr Ala Thr Met Leu Ala Trp Gly Ala Ile Glu Ser
 65                  70                  75                  80

Pro Glu Gly Tyr Ile Arg Ser Gly Gln Met Pro Tyr Leu Lys Asp Asn
                 85                  90                  95

Leu Arg Trp Val Asn Asp Tyr Phe Ile Lys Ala His Pro Ser Pro Asn
                100                 105                 110

Val Leu Tyr Val Gln Val Gly Asp Gly Asp Ala Asp His Lys Trp Trp
             115                 120                 125

Gly Pro Ala Glu Val Met Pro Met Glu Arg Pro Ser Phe Lys Val Asp
130                 135                 140

Pro Ser Cys Pro Gly Ser Asp Val Ala Ala Glu Thr Ala Ala Ala Met
145                 150                 155                 160

Ala Ala Ser Ser Ile Val Phe Ala Asp Asp Pro Ala Tyr Ala Ala
                 165                 170                 175

Thr Leu Val Gln His Ala Lys Gln Leu Tyr Thr Phe Ala Asp Thr Tyr
             180                 185                 190

Arg Gly Val Tyr Ser Asp Cys Val Pro Ala Gly Ala Phe Tyr Asn Ser
         195                 200                 205

Trp Ser Gly Tyr Gln Asp Glu Leu Val Trp Gly Ala Tyr Trp Leu Tyr
     210                 215                 220

Lys Val Thr Gly Asp Asp Ser Tyr Leu Ala Lys Ala Glu Tyr Glu Tyr
225                 230                 235                 240

Asp Phe Leu Ser Thr Gly Gln Gln Thr Asp Leu Arg Ser Tyr Arg Trp
                 245                 250                 255

Thr Ile Ala Trp Asp Asp Lys Ser Tyr Gly Thr Tyr Val Leu Leu Ala
             260                 265                 270

Lys Glu Thr Gly Lys Gln Lys Tyr Ile Asp Asp Ala Asn Arg Trp Leu
         275                 280                 285

Asp Tyr Trp Thr Val Gly Val Asn Gly Gln Arg Val Pro Tyr Ser Pro
     290                 295                 300

Gly Gly Met Ala Val Leu Asp Thr Trp Gly Ala Leu Arg Tyr Ala Ala
305                 310                 315                 320

Asn Thr Ala Phe Val Ala Leu Val Tyr Ala Lys Val Ile Asp Asp Pro
                 325                 330                 335

Val Arg Lys Gln Arg Tyr His Asp Phe Ala Val Arg Gln Ile Asn Tyr
             340                 345                 350

Ala Leu Gly Asp Asn Pro Arg Asn Ser Ser Tyr Val Val Gly Phe Gly
         355                 360                 365

Asn Asn Pro Pro Arg Asn Pro His His Arg Thr Ala His Gly Ser Trp
     370                 375                 380

Thr Asp Ser Ile Ala Ser Pro Ala Glu Asn Arg His Val Leu Tyr Gly
385                 390                 395                 400

Ala Leu Val Gly Gly Pro Gly Ser Pro Asn Asp Ala Tyr Thr Asp Asp
                 405                 410                 415

Arg Gln Asp Tyr Val Ala Asn Glu Val Ala Thr Asp Tyr Asn Ala Gly
             420                 425                 430

Phe Ser Ser Ala Leu Ala Met Leu Val Glu Glu Tyr Gly Gly Thr Pro
         435                 440                 445

Leu Ala Asp Phe Pro Pro Thr Glu Glu Pro Asp Gly Pro Glu Ile Phe
     450                 455                 460
```

```
Val Glu Ala Gln Ile Asn Thr Pro Gly Thr Thr Phe Thr Glu Ile Lys
465                 470                 475                 480

Ala Met Ile Arg Asn Gln Ser Gly Trp Pro Ala Arg Met Leu Asp Lys
            485                 490                 495

Gly Thr Phe Arg Tyr Trp Phe Thr Leu Asp Glu Gly Val Asp Pro Ala
        500                 505                 510

Asp Ile Thr Val Ser Ser Ala Tyr Asn Gln Cys Ala Thr Pro Glu Asp
    515                 520                 525

Val His His Val Ser Gly Asp Leu Tyr Tyr Val Glu Ile Asp Cys Thr
530                 535                 540

Gly Glu Lys Ile Phe Pro Gly Gly Gln Ser Glu His Arg Arg Glu Val
545                 550                 555                 560

Gln Phe Arg Ile Ala Gly Gly Pro Gly Trp Asp Pro Ser Asn Asp Trp
            565                 570                 575

Ser Phe Gln Gly Ile Gly Asn Glu Leu Ala Pro Ala Pro Tyr Ile Val
        580                 585                 590

Leu Tyr Asp Asp Gly Val Pro Val Trp Gly Thr Ala Pro Glu Glu Gly
    595                 600                 605

Glu Glu Pro Gly Gly Gly Glu Gly Pro Gly Gly Glu Glu Pro Gly
610                 615                 620

Glu Asp Val Thr Pro Pro Ser Ala Pro Gly Ser Pro Ala Val Arg Asp
625                 630                 635                 640

Val Thr Ser Thr Ser Ala Val Leu Thr Trp Ser Ala Ser Ser Asp Thr
            645                 650                 655

Gly Gly Ser Gly Val Ala Gly Tyr Asp Val Phe Leu Arg Ala Gly Thr
        660                 665                 670

Gly Gln Glu Gln Lys Val Gly Ser Thr Thr Arg Thr Ser Phe Thr Leu
    675                 680                 685

Thr Gly Leu Glu Pro Asp Thr Thr Tyr Ile Ala Ala Val Val Ala Arg
690                 695                 700

Asp Asn Ala Gly Asn Val Ser Gln Arg Ser Thr Val Ser Phe Thr Thr
705                 710                 715                 720

Leu Ala Glu Asn Gly Gly Pro Asp Ala Ser Cys Thr Val Gly Tyr
            725                 730                 735

Ser Thr Asn Asp Trp Asp Ser Gly Phe Thr Ala Ser Ile Arg Ile Thr
        740                 745                 750

Tyr His Gly Thr Ala Pro Leu Ser Ser Trp Glu Leu Ser Phe Thr Phe
    755                 760                 765

Pro Ala Gly Gln Gln Val Thr His Gly Trp Asn Ala Thr Trp Arg Gln
770                 775                 780

Asp Gly Ala Ala Val Thr Ala Thr Pro Met Ser Trp Asn Ser Ser Leu
785                 790                 795                 800

Ala Pro Gly Ala Thr Val Glu Val Gly Phe Asn Gly Ser Trp Ser Gly
            805                 810                 815

Ser Asn Thr Pro Pro Thr Asp Phe Thr Leu Asn Gly Glu Pro Cys Ala
        820                 825                 830

Leu Ala

<210> SEQ ID NO 2
<211> LENGTH: 2502
<212> TYPE: DNA
<213> ORGANISM: Thermobifida fusca
```

```
<400> SEQUENCE: 2
gaaccggcat tcaactacgc ggaagcactg caaaaatcca tgttcttcta cgaagctcaa      60
cgctcaggta aactgccgga aaataaccgt gtttcgtggc gcggtgatag cggtctgaac     120
gatggtgcag acgtcggcct ggatctgacc ggcggttggt atgatgccgg tgaccatgtg     180
aaatttggca tcccgatggc tttcaccgcg acgatgctgg cctggggtgc aattgaatct     240
ccggaaggtt atatccgcag tggccagatg ccgtacctga agataaccct gcgttgggtg     300
aatgactatt ttattaaagc gcatccgtct ccgaatgttc tgtacgttca agtcggtgac     360
ggcgatgccg accacaaatg gtggggtccg gcagaagtga tgccgatgga acgcccgagt     420
ttcaaagtcg atccgtcgtg cccgggcagc gacgtggcag cagaaaccgc agctgcgatg     480
gccgcaagct ctatcgtctt tgccgatgac gatccggcgt atgcggcaac cctggtgcag     540
cacgctaaac aactgtacac cttcgcggac acgtatcgtg gtgtctactc tgattgtgtg     600
ccggctggtg cgttttataa cagttggtcc ggctaccagg atgaactggt gtggggtgct     660
tattggctgt acaaagtgac cggcgacgat agctatctgg ccaaagcaga atatgaatac     720
gattttctga gcaccggaca gcaaacggat ctgcgtagct accgctggac cattgcgtgg     780
gacgataaaa gctatggcac ctatgtgctg ctggccaaag aaacgggcaa acagaaatat     840
atcgacgatg caaaccgctg gctggattac tggaccgtgg gtgttaatgg ccaacgtgtt     900
ccgtatagcc cgggcggtat ggccgtcctg gatacctggg gtgcactgcg ctatgccgca     960
aatacggctt cgtggcgcct ggtttacgcc aaagttattg acgatccggt ccgtaaacag    1020
cgctatcatg attttgctgt gcgccaaatc aactacgcgc tggtgataaa cccgcgtaat    1080
agttcctatg tggttggttt cggcaacaat ccgccgcgta atccgcatca ccgtaccgcg    1140
catggctcgt ggacggatag cattgcctct ccggcagaaa accgccacgt cctgtatggt    1200
gcactggtgg gcggtccggg ctccccgaat gacgcgtata ccgacgatcg tcaggattac    1260
gtggccaacg aagttgcaac ggattataat gccggctttt catcggctct ggcgatgctg    1320
gttgaagaat acggtggcac cccgctggca gactttccgc cgacggaaga accggatggt    1380
ccggaaattt cgttgaagc gcagatcaac accccgggca ccacgtttac ggaaattaaa    1440
gctatgatcc gtaatcaaag cggttggccg gcgcgcatgc tggacaaagg cacctttcgt    1500
tattggttca cgctggatga aggtgttgat ccggcggaca ttaccgttag ctctgcttac    1560
aaccagtgcg cgacgccgga agatgtccat cacgtgtccg gtgacctgta ttacgtggaa    1620
attgattgta ccggcgaaaa aatcttcccg ggcggtcaat cagaacatcg tcgcgaagtt    1680
caatttcgta tcgccggcgg tccgggttgg gacccgtcta acgactggag ttttcagggt    1740
attggcaatg aactggcccc ggcaccgtat atcgtgctgt acgacgatgg tgtcccggtg    1800
tggggcaccg caccggaaga aggcgaagaa ccgggcggtg gcgaaggtcc gggtggcggt    1860
gaagaaccgg gcgaagatgt caccccgccg tccgcaccgg gctcaccggc agttcgtgat    1920
gtcacctcaa cgtcggccgt tctaacctgg tccgcaagtt ccgacacggg cggttcaggc    1980
gtggctggct atgatgtttt cctgcgcgcg ggcaccggcc aggaacaaaa agtgggttct    2040
accacgcgta cgagttttac cctgacgggc ctggaaccgg ataccacgta tattgctgcg    2100
gtcgtggctc gcgataacgc gggtaatgtt agtcagcgtt ccaccgtctc attcaccacg    2160
ctggcagaaa acggcggtgg cccggatgca tcgtgcaccg ttggttatag cacgaatgat    2220
tgggactccg gctttaccgc ctcaattcgc atcacctatc atggcaccgc accgctgtca    2280
tcgtgggaac tgagttttac cttcccggct ggtcagcaag tgacccacgg ctggaatgcc    2340
```

-continued

```
acgtggcgtc aggatggtgc cgcagttacc gcgacgccga tgtcttggaa cagctctctg    2400
gctccgggtg caaccgttga agtcggtttt aatggcagtt ggagtggtag caacaccccg    2460
ccgaccgatt tcaccctgaa tggcgaaccg tgcgctctgg ca                       2502

<210> SEQ ID NO 3
<211> LENGTH: 46
<212> TYPE: PRT
<213> ORGANISM: Thermobifida fusca

<400> SEQUENCE: 3

Met Ser Val Thr Glu Pro Pro Arg Arg Gly Arg His Ser Arg
1               5                   10                  15

Ala Arg Arg Phe Leu Thr Ser Leu Gly Ala Thr Ala Ala Leu Thr Ala
                20                  25                  30

Gly Met Leu Gly Val Pro Leu Ala Thr Gly Thr Ala His Ala
            35                  40                  45

<210> SEQ ID NO 4
<211> LENGTH: 834
<212> TYPE: PRT
<213> ORGANISM: Thermobifida fusca

<400> SEQUENCE: 4

Glu Pro Ala Phe Asn Tyr Ala Glu Ala Leu Gln Lys Ser Met Phe Phe
1               5                   10                  15

Tyr Glu Ala Gln Arg Ser Gly Lys Leu Pro Glu Asn Asn Arg Val Ser
                20                  25                  30

Trp Arg Gly Asp Ser Gly Leu Asn Asp Gly Ala Asp Val Gly Leu Asp
            35                  40                  45

Leu Thr Gly Gly Trp Tyr Asp Ala Gly Asp His Val Lys Phe Gly Phe
        50                  55                  60

Pro Met Ala Phe Thr Ala Thr Met Leu Ala Trp Gly Ala Ile Glu Ser
65                  70                  75                  80

Pro Glu Gly Tyr Ile Arg Ser Gly Gln Met Pro Tyr Leu Lys Asp Asn
                85                  90                  95

Leu Arg Trp Val Asn Asp Tyr Phe Ile Lys Ala His Pro Ser Pro Asn
            100                 105                 110

Val Leu Tyr Val Gln Val Gly Asp Gly Asp Ala Asp His Lys Trp Trp
        115                 120                 125

Gly Pro Ala Glu Val Met Pro Met Glu Arg Pro Ser Phe Lys Val Asp
    130                 135                 140

Pro Ser Cys Pro Gly Ser Asp Val Ala Ala Glu Thr Ala Ala Ala Met
145                 150                 155                 160

Ala Ala Ser Ser Ile Val Phe Ala Asp Asp Pro Ala Tyr Ala Ala
                165                 170                 175

Thr Leu Val Gln His Ala Lys Gln Leu Tyr Thr Phe Ala Asp Thr Tyr
            180                 185                 190

Arg Gly Val Tyr Ser Asp Cys Val Pro Ala Gly Ala Phe Tyr Asn Ser
        195                 200                 205

Trp Ser Gly Tyr Gln Asp Glu Leu Val Trp Gly Ala Tyr Trp Leu Tyr
    210                 215                 220

Lys Ala Thr Gly Asp Asp Ser Tyr Leu Ala Lys Ala Glu Tyr Glu Tyr
225                 230                 235                 240

Asp Phe Leu Ser Thr Glu Gln Gln Thr Asp Leu Arg Ser Tyr Arg Trp
                245                 250                 255
```

-continued

```
Thr Ile Ala Trp Asp Asp Lys Ser Tyr Gly Thr Tyr Val Leu Leu Ala
            260                 265                 270

Lys Glu Thr Gly Lys Gln Lys Tyr Ile Asp Asp Ala Asn Arg Trp Leu
        275                 280                 285

Asp Tyr Trp Thr Val Gly Val Asn Gly Gln Arg Val Pro Tyr Ser Pro
    290                 295                 300

Gly Gly Met Ala Val Leu Asp Thr Trp Gly Ala Leu Arg Tyr Ala Ala
305                 310                 315                 320

Asn Thr Ala Phe Val Ala Leu Val Tyr Ala Lys Val Ile Asp Asp Pro
                325                 330                 335

Val Arg Lys Gln Arg Tyr His Asp Phe Ala Val Arg Gln Ile Asn Tyr
            340                 345                 350

Ala Leu Gly Asp Asn Pro Arg Asn Ser Ser Tyr Val Val Gly Phe Gly
        355                 360                 365

Asn Asn Pro Pro Arg Asn Pro His His Arg Thr Ala His Gly Ser Trp
    370                 375                 380

Thr Asp Ser Ile Ala Ser Pro Ala Glu Asn Arg His Val Leu Tyr Gly
385                 390                 395                 400

Ala Leu Val Gly Gly Pro Gly Ser Pro Asn Asp Ala Tyr Thr Asp Asp
                405                 410                 415

Arg Gln Asp Tyr Val Ala Asn Glu Val Ala Thr Asp Tyr Asn Ala Gly
            420                 425                 430

Phe Ser Ser Ala Leu Ala Met Leu Val Glu Glu Tyr Gly Gly Thr Pro
        435                 440                 445

Leu Ala Asp Phe Pro Pro Thr Glu Glu Pro Asp Gly Pro Glu Ile Phe
    450                 455                 460

Val Glu Ala Gln Ile Asn Thr Pro Gly Thr Thr Phe Thr Glu Ile Lys
465                 470                 475                 480

Ala Met Ile Arg Asn Gln Ser Gly Trp Pro Ala Arg Met Leu Asp Lys
                485                 490                 495

Gly Thr Phe Arg Tyr Trp Phe Thr Leu Asp Glu Gly Val Asp Pro Ala
            500                 505                 510

Asp Ile Thr Val Ser Ser Ala Tyr Asn Gln Cys Ala Thr Pro Glu Asp
        515                 520                 525

Val His His Val Ser Gly Asp Leu Tyr Tyr Val Glu Ile Asp Cys Thr
    530                 535                 540

Gly Glu Lys Ile Phe Pro Gly Gly Gln Ser Glu His Arg Arg Glu Val
545                 550                 555                 560

Gln Phe Arg Ile Ala Gly Gly Pro Gly Trp Asp Pro Ser Asn Asp Trp
                565                 570                 575

Ser Phe Gln Gly Ile Gly Asn Glu Leu Ala Pro Ala Pro Tyr Ile Val
            580                 585                 590

Leu Tyr Asp Asp Gly Val Pro Val Trp Gly Thr Ala Pro Glu Glu Gly
        595                 600                 605

Glu Glu Pro Gly Gly Gly Glu Gly Pro Gly Gly Glu Glu Pro Gly
    610                 615                 620

Glu Asp Val Thr Pro Pro Ser Ala Pro Gly Ser Pro Ala Val Arg Asp
625                 630                 635                 640

Val Thr Ser Thr Ser Ala Val Leu Thr Trp Ser Ala Ser Ser Asp Thr
                645                 650                 655

Gly Gly Ser Gly Val Ala Gly Tyr Asp Val Phe Leu Arg Ala Gly Thr
            660                 665                 670
```

```
Gly Gln Glu Gln Lys Val Gly Ser Thr Thr Arg Thr Ser Phe Thr Leu
            675                 680                 685

Thr Gly Leu Glu Pro Asp Thr Thr Tyr Ile Ala Ala Val Val Ala Arg
    690                 695                 700

Asp Asn Ala Gly Asn Val Ser Gln Arg Ser Thr Val Ser Phe Thr Thr
705                 710                 715                 720

Leu Ala Glu Asn Gly Gly Pro Asp Ala Ser Cys Thr Val Gly Tyr
            725                 730                 735

Ser Thr Asn Asp Trp Asp Ser Gly Phe Thr Ala Ser Ile Arg Ile Thr
            740                 745                 750

Tyr His Gly Thr Ala Pro Leu Ser Ser Trp Glu Leu Ser Phe Thr Phe
            755                 760                 765

Pro Ala Gly Gln Gln Val Thr His Gly Trp Asn Ala Thr Trp Arg Gln
            770                 775                 780

Asp Gly Ala Ala Val Thr Ala Thr Pro Met Ser Trp Asn Ser Ser Leu
785                 790                 795                 800

Ala Pro Gly Ala Thr Val Glu Val Gly Phe Asn Gly Ser Trp Ser Gly
            805                 810                 815

Ser Asn Thr Pro Pro Thr Asp Phe Thr Leu Asn Gly Glu Pro Cys Ala
            820                 825                 830

Leu Ala

<210> SEQ ID NO 5
<211> LENGTH: 612
<212> TYPE: PRT
<213> ORGANISM: Clostridium phytofermentans

<400> SEQUENCE: 5

Glu Thr Asn Tyr Asn Tyr Gly Glu Ala Leu Gln Lys Ser Ile Met Phe
1               5                   10                  15

Tyr Glu Phe Gln Arg Ser Gly Lys Leu Pro Ser Thr Ile Arg Asn Asn
            20                  25                  30

Trp Arg Gly Asp Ser Gly Leu Thr Asp Gly Ala Asp Val Gly Leu Asp
        35                  40                  45

Leu Thr Gly Gly Trp Tyr Asp Ala Gly Asp His Val Lys Phe Asn Leu
    50                  55                  60

Pro Leu Ala Tyr Thr Val Thr Met Leu Ala Trp Ala Val Tyr Glu Glu
65              70                  75                  80

Glu Ala Thr Leu Ser Lys Ala Gly Gln Leu Ser Tyr Leu Leu Asp Glu
            85                  90                  95

Ile Lys Trp Ser Ser Asp Tyr Leu Ile Lys Cys His Pro Gln Ala Asn
            100                 105                 110

Val Phe Tyr Tyr Gln Val Gly Asn Gly Asn Thr Asp His Ser Trp Trp
            115                 120                 125

Gly Pro Ala Glu Val Met Gln Met Ala Arg Pro Ser Tyr Lys Val Asp
        130                 135                 140

Leu Asn Asn Pro Gly Ser Thr Val Val Gly Glu Ala Ala Ala Leu
145                 150                 155                 160

Ala Ala Thr Ala Leu Ile Tyr Lys Thr Lys Asp Pro Thr Tyr Ser Ala
            165                 170                 175

Thr Cys Leu Arg His Ala Lys Glu Leu Phe Asn Phe Ala Asp Thr Thr
            180                 185                 190

Lys Ser Asp Ala Gly Tyr Thr Ala Ala Ser Gly Phe Tyr Thr Ser Tyr
        195                 200                 205
```

-continued

```
Ser Gly Phe Tyr Asp Glu Leu Ser Trp Ala Ala Thr Trp Ile Tyr Leu
210                 215                 220
Ala Ser Gly Glu Ala Thr Tyr Leu Asp Lys Ala Glu Ser Tyr Val Ala
225                 230                 235                 240
Lys Trp Gly Thr Glu Pro Gln Ser Ser Thr Leu Ser Tyr Lys Trp Ala
                    245                 250                 255
Gln Asn Trp Asp Asp Val His Tyr Gly Ala Ala Leu Leu Leu Ala Arg
                260                 265                 270
Ile Thr Asn Lys Ala Ile Tyr Lys Asn Asn Ile Glu Met His Leu Asp
            275                 280                 285
Tyr Trp Thr Thr Gly Tyr Asn Gly Ser Arg Ile Thr Tyr Thr Pro Lys
290                 295                 300
Gly Leu Ala Trp Leu Asp Ser Trp Gly Ala Leu Arg Tyr Ala Thr Thr
305                 310                 315                 320
Thr Ala Phe Leu Ala Ser Val Tyr Ala Asp Trp Ser Gly Cys Ser Ala
                325                 330                 335
Gly Lys Val Ser Thr Tyr Asn Ala Phe Ala Lys Gln Gln Val Asp Tyr
                340                 345                 350
Ala Leu Gly Ser Thr Gly Arg Ser Phe Val Val Gly Tyr Gly Val Asn
                355                 360                 365
Ser Pro Thr Arg Pro His His Arg Thr Ala His Ser Ser Trp Ala Asp
370                 375                 380
Ser Gln Thr Glu Pro Asn Tyr His Arg His Thr Ile Tyr Gly Ala Leu
385                 390                 395                 400
Val Gly Gly Pro Gly Asn Asn Asp Ser Tyr Glu Asp Asn Ile Asn Asn
                405                 410                 415
Tyr Val Asn Asn Glu Ile Ala Cys Asp Tyr Asn Ala Gly Phe Val Gly
                420                 425                 430
Ala Leu Ala Lys Val Tyr Lys Thr Tyr Gly Gly Thr Pro Ile Ala Asn
                435                 440                 445
Phe Lys Ala Ile Glu Thr Val Thr Asn Asp Glu Leu Phe Ile Gln Ala
450                 455                 460
Gly Ile Asn Ala Ser Gly Pro Ser Phe Ile Glu Val Lys Ala Leu Val
465                 470                 475                 480
Phe Asn Glu Thr Gly Trp Pro Ala Arg Val Thr Asp Lys Leu Ser Phe
                485                 490                 495
Lys Tyr Phe Ile Asp Ile Ser Glu Tyr Val Ala Lys Gly Tyr Thr Lys
                500                 505                 510
Asn Asp Phe Thr Val Ser Thr Asn Tyr Asn Asn Gly Ala Thr Thr Ser
                515                 520                 525
Ala Leu Leu Pro Trp Asp Ala Ala Asn Asn Ile Tyr Tyr Val Asn Val
                530                 535                 540
Asp Phe Ser Gly Thr Lys Ile Tyr Pro Gly Gly Gln Ser Ala Tyr Lys
545                 550                 555                 560
Lys Glu Val Gln Phe Arg Ile Ala Gly Pro Gln Asn Val Asn Ile Trp
                565                 570                 575
Asp Asn Ser Asn Asp Tyr Ser Phe Thr Gln Ile Ala Asn Val Ser Ser
                580                 585                 590
Gly Asn Thr Val Lys Thr Thr Tyr Ile Pro Leu Tyr Asp Asn Gly Lys
            595                 600                 605
Leu Val Phe Gly
610
```

```
<210> SEQ ID NO 6
<211> LENGTH: 834
<212> TYPE: PRT
<213> ORGANISM: Thermobifida fusca

<400> SEQUENCE: 6

Glu Pro Ala Phe Asn Tyr Ala Glu Ala Leu Gln Lys Ser Met Phe Phe
1               5                   10                  15

Tyr Glu Ala Gln Arg Ser Gly Lys Leu Pro Glu Asn Asn Arg Val Ser
                20                  25                  30

Trp Arg Gly Asp Ser Gly Leu Asn Asp Gly Ala Asp Val Gly Leu Asn
            35                  40                  45

Leu Thr Gly Gly Trp Tyr Asp Ala Gly Asp His Val Lys Phe Gly Phe
        50                  55                  60

Pro Met Ala Phe Thr Ala Thr Met Leu Ala Trp Gly Ala Ile Glu Ser
65                  70                  75                  80

Pro Glu Gly Tyr Ile Arg Ser Gly Gln Met Pro Tyr Leu Lys Asp Asn
                85                  90                  95

Leu Arg Trp Val Asn Asp Tyr Phe Ile Lys Ala His Ser Ser Pro Asn
            100                 105                 110

Val Leu Tyr Val Gln Val Gly Asp Gly Asp Ala Asp His Lys Trp Trp
        115                 120                 125

Gly Pro Ala Glu Val Met Pro Met Glu Arg Pro Ser Phe Lys Val Asp
130                 135                 140

Pro Ser Cys Pro Gly Ser Asp Val Ala Ala Glu Thr Ala Ala Ala Met
145                 150                 155                 160

Ala Ala Ser Ser Ile Val Phe Ala Asp Asp Pro Ala Tyr Ala Ala
                165                 170                 175

Thr Leu Val Gln His Ala Lys Gln Leu Tyr Thr Phe Ala Asp Thr Tyr
            180                 185                 190

Arg Gly Val Tyr Ser Asp Cys Val Pro Ala Ser Ala Phe Tyr Asn Ser
        195                 200                 205

Trp Ser Gly Tyr Gln Asp Glu Leu Val Trp Gly Ala Tyr Trp Leu Tyr
    210                 215                 220

Lys Ala Thr Gly Asp Asp Ser Tyr Leu Ala Lys Ala Glu Tyr Glu Tyr
225                 230                 235                 240

Asp Phe Leu Ser Thr Glu Gln Thr Asp Leu Arg Ser Tyr Arg Trp
                245                 250                 255

Thr Ile Ala Trp Asp Asp Lys Ser Tyr Gly Thr Tyr Val Leu Leu Ala
            260                 265                 270

Lys Glu Thr Gly Lys Gln Lys Tyr Ile Asp Asp Ala Asn Arg Trp Leu
        275                 280                 285

Asp Tyr Trp Thr Val Gly Val Asn Gly Gln Arg Val Pro Tyr Ser Pro
    290                 295                 300

Gly Gly Met Ala Val Leu Asp Thr Trp Gly Ala Leu Arg Tyr Ala Ala
305                 310                 315                 320

Asn Thr Ala Phe Val Ala Leu Val Tyr Ala Lys Val Ile Asp Asp Pro
                325                 330                 335

Val Arg Lys Gln Arg Tyr His Asp Phe Ala Val Arg Gln Ile Asn Tyr
            340                 345                 350

Ala Leu Gly Asp Asn Pro Arg Asn Ser Ser Tyr Val Val Gly Phe Gly
        355                 360                 365

Asn Asn Pro Pro Arg Asn Pro His His Arg Thr Ala His Gly Ser Trp
    370                 375                 380
```

-continued

```
Thr Asp Ser Ile Ala Ser Pro Ala Glu Asn Arg His Val Leu Tyr Gly
385                 390                 395                 400

Ala Leu Val Gly Gly Pro Gly Ser Pro Asn Asp Ala Tyr Thr Asp Asp
            405                 410                 415

Arg Gln Asp Tyr Val Ala Asn Glu Val Ala Thr Asp Tyr Asn Ala Gly
        420                 425                 430

Phe Ser Ser Ala Leu Ala Met Leu Val Glu Glu Tyr Gly Gly Thr Pro
    435                 440                 445

Leu Ala Asp Phe Pro Pro Thr Glu Glu Pro Asp Gly Pro Glu Ile Phe
450                 455                 460

Val Glu Ala Gln Ile Asn Thr Pro Gly Thr Thr Phe Thr Glu Ile Lys
465                 470                 475                 480

Ala Met Ile Arg Asn Gln Ser Gly Trp Pro Ala Arg Met Leu Asp Lys
            485                 490                 495

Gly Thr Phe Arg Tyr Trp Phe Thr Leu Asp Glu Gly Val Asp Pro Ala
        500                 505                 510

Asp Ile Thr Val Ser Ser Ala Tyr Asn Gln Cys Ala Thr Pro Glu Asp
    515                 520                 525

Val His His Val Ser Gly Asp Leu Tyr Tyr Val Glu Ile Asp Cys Thr
530                 535                 540

Gly Glu Lys Ile Phe Pro Gly Gly Gln Ser Glu His Arg Arg Glu Val
545                 550                 555                 560

Gln Phe Arg Ile Ala Gly Gly Pro Gly Trp Asp Pro Ser Asn Asp Trp
            565                 570                 575

Ser Phe Gln Gly Ile Gly Asn Glu Leu Ala Pro Ala Pro Tyr Ile Val
        580                 585                 590

Leu Tyr Asp Asp Gly Val Pro Val Trp Gly Thr Ala Pro Glu Glu Gly
    595                 600                 605

Glu Glu Pro Gly Gly Gly Glu Gly Pro Gly Gly Glu Glu Pro Gly
610                 615                 620

Glu Asp Val Thr Pro Pro Ser Ala Pro Gly Ser Pro Ala Val Arg Asp
625                 630                 635                 640

Val Thr Ser Thr Ser Ala Val Leu Thr Trp Ser Ala Ser Ser Asp Thr
            645                 650                 655

Gly Gly Ser Gly Val Ala Gly Tyr Asp Val Phe Leu Arg Ala Gly Thr
        660                 665                 670

Gly Gln Glu Gln Lys Val Gly Ser Thr Arg Thr Ser Phe Thr Leu
    675                 680                 685

Thr Gly Leu Glu Pro Asp Thr Thr Tyr Ile Ala Ala Val Val Ala Arg
690                 695                 700

Asp Asn Ala Gly Asn Val Ser Gln Arg Ser Thr Val Ser Phe Thr Thr
705                 710                 715                 720

Leu Ala Glu Asn Gly Gly Pro Asp Ala Ser Cys Thr Val Gly Tyr
            725                 730                 735

Ser Thr Asn Asp Trp Asp Ser Gly Phe Thr Ala Ser Ile Arg Ile Thr
        740                 745                 750

Tyr His Gly Thr Ala Pro Leu Ser Ser Trp Glu Leu Ser Phe Thr Phe
    755                 760                 765

Pro Ala Gly Gln Gln Val Thr His Gly Trp Asn Ala Thr Trp Arg Gln
770                 775                 780

Asp Gly Thr Ala Val Thr Ala Pro Met Ser Trp Asn Ser Ser Leu
785                 790                 795                 800
```

Ala Pro Gly Ala Thr Val Glu Val Gly Phe Asn Gly Ser Trp Ser Gly
              805                 810                 815

Ser Asn Thr Pro Pro Thr Asp Phe Thr Leu Asn Gly Glu Pro Cys Ala
            820                 825                 830

Leu Ala

<210> SEQ ID NO 7
<211> LENGTH: 834
<212> TYPE: PRT
<213> ORGANISM: Thermobifida fusca

<400> SEQUENCE: 7

Glu Pro Ala Phe Asn Tyr Ala Glu Ala Leu Gln Lys Ser Met Phe Phe
1               5                   10                  15

Tyr Glu Ala Gln Arg Ser Gly Lys Leu Pro Glu Asn Asn Arg Val Ser
            20                  25                  30

Trp Arg Gly Asp Ser Gly Leu Asn Asp Gly Ala Asp Val Gly Leu Asp
        35                  40                  45

Leu Thr Gly Gly Trp Tyr Asp Ala Gly Asp His Val Lys Phe Gly Phe
    50                  55                  60

Pro Met Ala Phe Thr Ala Thr Met Leu Ala Trp Gly Ala Ile Glu Ser
65                  70                  75                  80

Pro Glu Gly Tyr Ile Arg Ser Gly Gln Met Pro Tyr Leu Lys Asp Asn
                85                  90                  95

Leu Arg Trp Val Asn Asp Tyr Phe Ile Lys Ala His Pro Ser Pro Asn
            100                 105                 110

Val Leu Tyr Val Gln Val Gly Asp Gly Asp Ala Asp His Lys Trp Trp
        115                 120                 125

Gly Pro Ala Glu Val Met Pro Met Glu Arg Pro Ser Phe Lys Val Asp
    130                 135                 140

Pro Ser Cys Pro Gly Ser Asp Val Ala Ala Glu Thr Ala Ala Ala Met
145                 150                 155                 160

Ala Ala Ser Ser Ile Val Phe Ala Asp Asp Asp Pro Ala Tyr Ala Ala
                165                 170                 175

Thr Leu Val Gln His Ala Lys Gln Leu Tyr Thr Phe Ala Asp Thr Tyr
            180                 185                 190

Arg Gly Val Tyr Ser Asp Cys Val Pro Ala Gly Ala Phe Tyr Asn Ser
        195                 200                 205

Trp Ser Gly Tyr Gln Asp Glu Leu Val Trp Gly Ala Tyr Trp Leu Tyr
    210                 215                 220

Lys Ala Thr Gly Asp Asp Ser Tyr Leu Ala Lys Ala Glu Tyr Glu Tyr
225                 230                 235                 240

Asp Phe Leu Ser Thr Glu Gln Gln Thr Asp Leu Arg Ser Tyr Arg Trp
                245                 250                 255

Thr Ile Ala Trp Asp Asp Lys Ser Tyr Gly Thr Tyr Val Leu Leu Ala
            260                 265                 270

Lys Glu Thr Gly Lys Gln Lys Tyr Ile Asp Asp Ala Asn Arg Trp Leu
        275                 280                 285

Asp Tyr Trp Thr Val Gly Val Asn Gly Gln Arg Val Pro Tyr Ser Pro
    290                 295                 300

Gly Gly Met Ala Val Leu Asp Thr Trp Gly Ala Leu Arg Tyr Ala Ala
305                 310                 315                 320

Asn Thr Ala Phe Val Ala Leu Val Tyr Ala Lys Val Ile Asp Asp Pro
                325                 330                 335

```
Val Arg Lys Gln Arg Tyr His Asp Phe Ala Val Arg Gln Ile Asn Tyr
            340                 345                 350

Ala Leu Gly Asp Asn Pro Arg Asn Ser Ser Tyr Val Val Gly Phe Gly
            355                 360                 365

Asn Asn Pro Pro Arg Asn Pro His His Arg Thr Ala His Gly Ser Trp
370                 375                 380

Thr Asp Ser Ile Ala Ser Pro Ala Glu Asn Arg His Val Leu Tyr Gly
385                 390                 395                 400

Ala Leu Val Gly Gly Pro Gly Ser Pro Asn Asp Ala Tyr Thr Asp Asp
                405                 410                 415

Arg Gln Asp Tyr Val Ala Asn Glu Val Ala Thr Asp Tyr Asn Ser Gly
            420                 425                 430

Phe Ser Ser Ala Leu Ala Met Leu Val Glu Glu Tyr Gly Gly Thr Pro
            435                 440                 445

Leu Ala Asp Phe Pro Pro Thr Glu Glu Pro Asp Gly Pro Glu Ile Phe
            450                 455                 460

Val Glu Ala Gln Ile Asn Thr Pro Gly Thr Thr Phe Thr Glu Ile Lys
465                 470                 475                 480

Ala Met Ile Arg Asn Gln Ser Gly Trp Pro Ala Arg Met Leu Asp Lys
                485                 490                 495

Gly Thr Phe Arg Tyr Trp Phe Thr Leu Asp Glu Gly Val Asp Pro Ala
            500                 505                 510

Asp Ile Thr Val Ser Ser Ala Tyr Asn Gln Cys Ala Thr Pro Glu Asp
            515                 520                 525

Val His His Val Ser Gly Asp Leu Tyr Tyr Val Glu Ile Asp Cys Thr
            530                 535                 540

Gly Glu Lys Ile Phe Pro Gly Gly Gln Ser Glu His Arg Arg Glu Val
545                 550                 555                 560

Gln Phe Arg Ile Ala Gly Gly Pro Gly Trp Asp Pro Ser Asn Asp Trp
                565                 570                 575

Ser Phe Gln Gly Ile Gly Asn Glu Leu Ala Pro Ala Pro Tyr Ile Val
            580                 585                 590

Leu Tyr Asn Asp Gly Val Pro Val Trp Gly Thr Ala Pro Glu Glu Gly
            595                 600                 605

Glu Glu Pro Gly Gly Gly Glu Gly Pro Gly Gly Glu Glu Pro Gly
            610                 615                 620

Glu Asp Val Thr Pro Pro Ser Ala Pro Gly Ser Pro Ala Val Arg Asp
625                 630                 635                 640

Val Thr Ser Thr Ser Ala Val Leu Thr Trp Ser Ala Ser Ser Asp Thr
                645                 650                 655

Gly Gly Ser Gly Val Ala Gly Tyr Asp Val Phe Leu Arg Ala Gly Thr
            660                 665                 670

Gly Gln Glu Gln Lys Val Gly Ser Thr Thr Arg Thr Ser Phe Thr Leu
            675                 680                 685

Thr Gly Leu Glu Pro Asp Thr Thr Tyr Ile Ala Ala Val Val Ala Arg
            690                 695                 700

Asp Asn Ala Gly Asn Val Ser Gln Arg Ser Thr Val Ser Phe Thr Thr
705                 710                 715                 720

Leu Ala Glu Asn Gly Gly Pro Asp Ala Ser Cys Thr Val Gly Tyr
                725                 730                 735

Ser Thr Asn Asp Trp Asp Ser Gly Phe Thr Ala Ser Ile Arg Phe Thr
            740                 745                 750
```

```
                                        -continued

Tyr His Gly Thr Ala Ser Leu Ser Ser Trp Glu Leu Ser Phe Thr Phe
        755                 760                 765

Pro Ala Gly Gln Gln Val Thr His Gly Trp Asn Ala Thr Trp Arg Gln
    770                 775                 780

Asp Gly Ala Ala Val Thr Ala Thr Pro Met Ser Trp Asn Ser Ser Leu
785                 790                 795                 800

Ala Pro Gly Ala Thr Val Glu Val Gly Phe Asn Gly Ser Trp Ser Gly
                805                 810                 815

Ser Asn Thr Pro Pro Thr Asp Phe Thr Leu Asn Gly Glu Pro Cys Ala
            820                 825                 830

Leu Ala

<210> SEQ ID NO 8
<211> LENGTH: 39
<212> TYPE: DNA
<213> ORGANISM: Artificial Sequence
<220> FEATURE:
<223> OTHER INFORMATION: ARTIFICIAL DNA PRIMER

<400> SEQUENCE: 8
tacttccaat ccaatgcaat ggaaccggca ttcaactac                         39

<210> SEQ ID NO 9
<211> LENGTH: 36
<212> TYPE: DNA
<213> ORGANISM: Artificial Sequence
<220> FEATURE:
<223> OTHER INFORMATION: ARTIFICIAL DNA PRIMER

<400> SEQUENCE: 9
ttatccactt ccaatgttat tatgccagag cgcacg                            36
```

CELLULASE VARIANTS

CROSS-REFERENCE TO RELATED APPLICATIONS

This application is a 35 U.S.C. 371 national application of PCT/US2012/033138 filed on Apr. 11, 2012, which claims priority or the benefit under 35 U.S.C. 119 of U.S. Provisional. Application No. 61/474,633 filed on Apr. 12, 2011, the contents of which are fully incorporated herein by reference.

STATEMENT OF GOVERNMENTAL SUPPORT

This work was supported in part by Grant No DE-SC0002302 from the Department of Energy. The Government has certain rights in this invention.

FIELD OF THE INVENTION

The present invention relates to cellulolytic enzymes useful in the processing of plant biomass and other cellulosic materials.

BACKGROUND OF THE INVENTION

Cellulases or cellulolytic enzymes are enzymes involved in hydrolysis of cellulose. Typically there are three major types of cellulase enzymes involved in the hydrolysis of native cellulose, namely cellobiohydrolase (1,4-beta-D-glucan cellobiohydrolase, EC 3.2.1.91), endo-beta-1,4-glucanase (endo-1,4-beta-D-glucan 4-glucanohydrolase, EC 3.2.1.4) and beta-glucosidase (EC 3.2.1.21).

The endo-beta-1,4-glucanases (EC No. 3.2.1.4) constitute a group of hydrolases of particular interest in various industrial applications. Endoglucanases catalyse endo hydrolysis of 1,4-beta-D-glycosidic linkages in cellulose, cellulose derivatives (such as carboxy methyl cellulose and hydroxy ethyl cellulose), lichenin, beta-1,4 bonds in mixed beta-1,3 glucans such as cereal beta-D-glucans or xyloglucans, and other plant material containing cellulosic components Cellulases are synthesized by a large number of microorganisms that include, for example, fungi, actinomycetes, myxobacteria and true bacteria, and certain plants. Endoglucanases of a wide variety of specificities have been identified.

One industrial use of cellulolytic enzymes is for treatment of cellulosic textiles or fabrics, e.g., as ingredients in detergent compositions or fabric softener compositions, for biopolishing of new fabrics (garment finishing), and for obtaining a "stone-washed" look of cellulose-containing fabrics, especially denim. Another important industrial use of cellulolytic enzymes is the use for treatment of paper pulp, e.g., for improving the drainage or for deinking of recycled paper.

Bioconversion of renewable lignocellulosic biomass to a fermentable sugar that is subsequently fermented to produce alcohol (e.g., ethanol) or other fuels as an alternative to petroleum-based fuels is also an important use of cellulosic enzymes. Fermentable sugars are also used to produce plastics, polymers and other bio-based products and this industry is expected to grow substantially increasing the demand for abundant low cost fermentable sugars that can be used as a feed stock in lieu of petroleum based feedstocks. Cellulosic biomass is the most abundant renewable natural resource. Generated at a rate of ~100 billion dry tons/year by the biosphere, cellulosic biomass has the potential to replace the world's demand for diminishing fossil fuels.

The major polysaccharides comprising different lignocellulosic residues, that may be considered as a potential renewable feedstock, include, for example, cellulose and hemicelluloses (xylans). The enzymatic hydrolysis of these polysaccharides to soluble sugars, for example glucose, xylose, arabinose, galactose, mannose, and other hexoses and pentoses can occur under the action of different enzymes acting in concert. Endo-1,4-β-glucanases (EG) and exo-cellobiohydrolases (CBH) catalyze the hydrolysis of insoluble cellulose to cellooligosaccharides (cellobiose as a main product), while β-glucosidases (BGL) convert the oligosaccharides to glucose. Xylanases together with other accessory enzymes (non-limiting examples of which include α-L-arabinofuranosidases, feruloyl and acetylxylan esterases, glucuronidases, and (β-xylosidases) catalyze the hydrolysis of hemicelluloses.

Regardless of the type of cellulosic feedstock, the cost and hydrolytic efficiency of enzymes are major factors that restrict the commercialization of the biomass bioconversion processes. According to Zhang, Y. H. P., "[o]ne of the most important and difficult technological challenges is to overcome the recalcitrance of natural lignocellulosic materials, which must be enzymatically hydrolyzed to produce fermentable sugars" (see, Zhang et al. (2006) *Biotechnol. Adv.* 24: 452-481). A major limitation for the conversion of biomass to biofuel and renewable chemicals is the high cost and large quantities of enzymes required for hydrolysis.

SUMMARY

In various embodiments novel variant cellulolytic enzymes are provided having improved activity and/or stability. In certain embodiments the variant cellulotyic enzymes comprise a glycoside hydrolase consisting of or comprising a substitution at one or more positions corresponding to one or more of residues F64, A226, and/or E246 in *Thermobifida fusca* Cel9A enzyme. In certain embodiments the enzyme comprises no more than 5, additional variations, or no more than 4 additional variations, or no more than three additional variations, or no more than two additional variations, or no more than one additional variation at positions other than those corresponding to F64, A226, and/or E246 in *Thermobifida fusca* Cel9A. In certain embodiments the glycoside hydrolase is a variant of a family 9 glycoside hydrolase. In certain embodiments the glycoside hydrolase is a variant of a theme B glycoside hydrolase. In certain embodiments the variant comprises a substitution at a position corresponding to F64 in *Thermobifida fusca* Cel9A. In certain embodiments the variant comprises a substitution at a position corresponding to A226 in *Thermobifida fusca* Cel9A. In certain embodiments the variant comprises a substitution at a position corresponding to E246 in *Thermobifida fusca* Cel9A. In certain embodiments the variant comprises a substitution at positions corresponding to F64 and A226 in *Thermobifida fusca* Cel9A. In certain embodiments the variant comprises a substitution at positions corresponding to F64 and E246 in *Thermobifida fusca* Cel9A. In certain embodiments the variant comprises a substitution at positions corresponding to A226 and E246 in *Thermobifida fusca* Cel9A. In certain embodiments the variant comprises a substitution at positions corresponding to F64, A226, and E246 in *Thermobifida fusca* Cel9A. In certain embodiments the substitution at a position corresponding position F64 in *Thermobifida fusca* Cel9A is a substitution to I, V, L, or M. In certain embodiments the substitution at a position corresponding position F64 in *Thermobifida fusca* Cel9A is a substitution to I. In certain embodiments the substitution at a position corresponding position A226 in *Thermobifida fusca* Cel9A is a substitution to V, I, L, M, or T. In certain embodiments the substitution at a position corresponding position A226 in *Thermobifida fusca* Cel9A is a substitution to V, I, L, or M. In certain embodiments the substitution at a position corresponding position A226 in *Thermobifida fusca* Cel9A is a substitution to V. In certain embodiments the substitution at a position corresponding position E246 in *Thermobifida fusca* Cel9A is a substitution to G, A, N, or S. In certain embodiments the substitution at a position corresponding position E246 in *Thermobifida fusca* Cel9A is a substitution to G. In certain embodiments the enzyme is a variant of a glycoside hydrolase from an organism selected from the group consisting of archaea, bacteria, and eukaryota. In certain embodiments the enzyme is a variant of a glycoside hydrolase from a gram negative bacterium. In certain embodiments the enzyme is a variant of a glycoside hydrolase from a gram positive bacterium. In certain embodiments the enzyme is a variant of glycoside hydrolase from a bacterial family selected from the group consisting of Thermofidia, Micromonospora, Cellulomonas, Listeria, Pseudomonas, Ruminococcus, Saccharophagus, Streptomyces, Vibrio, Xanthomonas, and Clostridium. In certain embodiments the enzyme is a variant of *Thermobifida fusca* Cel9A. In certain embodiments the enzyme is a variant of *Clostridium phytofermentans* Cphy3367.

Variant cellulolytic enzymes, as contemplated herein, do not include any wild-type and/or naturally occurring enzymes. In certain embodiments the enzyme has at least 50%, or at least 60%, or at least 65%, or at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99% sequence identity with F1, and/or Cel9A, and/or Cphy3367, and/or G03, and/or G11. In certain embodiments the enzyme is attached to or operably linked to a signal peptide. In certain embodiments the cellulolytic enzyme is present and/or displayed on the surface of an organism selected from the group consisting of a phage, a fungus, an alga, and a bacterium. In certain embodiments the cellulolytic enzyme is present and/or displayed on a substrate or the surface of a particle (e.g., a particle comprising a material selected from the group consisting of a plastic, a glass, a mineral, a synthetic polymer, a biological polymer, and a metal). In certain embodiments the substrate or particle comprises a surface of a microfluidic channel or chamber, a surface of a bioreactor, or a surface of a bioreactor. In certain embodiments the cellulolytic enzyme is a component of a cellulosome or a minicellulosome. In certain embodiments the cellulosome is on the surface of a yeast, bacteria, or non-yeast fungus. In certain embodiments cellulosome comprises one or more additional enzymes selected from the group consisting of an endocellulase, an exocellulase, a beta-glucosidase (cellobiase), an oxidative cellulose, a xylanase, a hemicellulase, a lichenase, a chitenase, a xylanase, a cellulose phosphorylase, and a cellulose disrupting protein.

In various embodiments nucleic acid encoding the variant enzymes, vectors comprising the nucleic acids and host cells transfected to produce the variant enzymes are also provided. In certain embodiments the nucleic acid comprises codons optimized for expression in a host cell (e.g., optimized for expression in a host selected from the group consisting of a bacterium, a yeast, a fungus, an alga, an insect, and a mammalian cell). In certain embodiments the nucleic acid comprises codons optimized for expression in *E. coli*. In certain embodiments the host cell is selected from the group consisting of an archiobacterium, a bacterium, a yeast cell, a fungal cell, an algal cell, a plant cell, an insect cell, and a mammalian cell.

In various embodiments a method of producing a cellulase is provided where the method comprises a) culturing a host cell comprising a nucleic acid that encodes a cellulase as described herein in a suitable culture medium under suitable conditions to produce cellulase; and obtaining the produced cellulase.

A method of producing an enzyme variant is provided that comprises introducing a substitution in the amino acid sequence of an endoglucanase at one or more positions corresponding to one or more of residues F64, A226, and/or E246 in *Thermobifida fusca* Cel9A.

Also provided are methods of degrading cellulosic biomass into fermentable sugars. The methods typically involve contacting the cellulosic biomass with a cellulolytic enzyme variant as described herein under conditions in which the enzyme partially or fully degrades cellulose in said cellulosic biomass to form one or more fermentable sugars. In certain embodiments the cellulosic biomass comprises one or more materials selected from the group consisting of an agricultural plant waste (e.g., corn stover, cereal straw, sugarcane bagasse), a plant waste from an industrial processes (e.g., sawdust, paper pulp), an a non-food energy crop (e.g., switchgrass). In certain embodiments the cellulosic biomass comprises one or more materials selected form the group consisting of grasses, rice hulls, bagasse, jute, hemp, flax, bamboo, sisal, abaca, straw, corn cobs, corn stover, alfalfa, hay, coconut hair, seaweed, and algae.

In certain embodiments a cellulolytic compositions is provided where the composition comprises a plurality of cellulolytic enzymes at least one of which is an enzyme variant as described herein. In certain embodiments the composition comprise a second enzyme selected from the group consisting of an endocellulase, an exocellulase, a beta-glucosidase (cellobiase), an oxidative cellulose, a xylanase, a hemicellulase, a lichenase, a chitenase, a xylanase, and a cellulose phosphorylase.

Also provided is a detergent composition comprising a cellulolytic enzyme variant as described herein, and a surfactant. In certain embodiments the detergent comprises a laundry detergent, a dish detergent, or an industrial detergent.

Uses of the variant cellulolytic enzymes described herein are also provided. Such uses include, but are not limited to methods of processing textiles, or paper, and methods of processing cellulosic stock materials (e.g., lignocellulolytic materials) to produce sugars, alcohols, and/or other compounds, and the like. In certain embodiments such uses include, but are not limited to the treatment of a cellulose containing textile, stone washing or dying of a fabric, the treatment of wood pulp or other lignocellulosic material, and the reduction of biomass to glucose.

Definitions

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Preferred "peptides", "polypeptides", and "proteins" are chains of amino acids whose alpha carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

A "variant enzyme" refers to an enzyme that is derived from a precursor enzyme (e.g., the native enzyme, or a previously known variant) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, or insertion of one or more amino acids at one or more sites in the amino acid sequence. In one embodiment, the preparation of an enzyme variant can be achieved by preparing a nucleic acid sequence (e.g., by modifying a DNA sequence that encodes for the native protein), transformation of that nucleic acid sequence into a suitable host, and expression of the modified sequence to form the variant. In another illustrative embodiment, the enzyme variant may also be prepared by expressing the DNA sequence in an in vitro expression system without the need for a host. In certain embodiments the variant enzyme can be chemically synthesized.

The term "family 9 glycoside hydrolase" refers to a family of cellulolytic enzymes characterized by a catalytic domain structure having an $(a/a)_6$ barrel fold that contains an open active site cleft that contains at least six sugar binding subsites −4 to +2. In processive endoglucanases the catalytic domain is joined to a family 3c carbohydrate-binding module that is aligned with the active site cleft. Sequence-based algorithmic methods are used to assign enzymes to various families. The glycoside hydrolases have been classified into more than 100 families. Each family (GH family) contains proteins that are related by sequence, and by corollary, fold (see Henrissat (1991) *Biochem J.* 280:309-316).

A theme B subfamily of said "family 9 glycoside hydrolase" refers to enzymes in which the catalytic module is fused to a family 3 carbohydrate-binding module (see Gilad et al. (2003) *J Bacteriol* 185:391-398)

The term "cellulosic biomass" refers to plant, algal, or other biomass that contains cellulose.

Lignocellulosic biomass refers to plant biomass that typically contains cellulose, hemicellulose, and lignin. The carbohydrate polymers (cellulose and hemicelluloses) are often tightly bound to the lignin. Lignocellulosic biomass can be grouped into four main categories: (1) agricultural residues (including corn stover and sugarcane bagasse), (2) dedicated energy crops, (3) wood residues (including sawmill and paper mill discards), and (4) municipal paper waste. Illustrative lignocellulosic biomass sources include, but are not limited to grasses, rice hulls, bagasse, jute, hemp, flax, bamboo, sisal, abaca, straw, corn cobs, corn stover, alfalfa, hay, coconut hair, seaweed, algae, A cellulase is an enzyme that breaks down cellulose, especially in the wall structures, and a "cellulosome" is an array, cluster, or sequence of enzymes or cellulases that degrades cellulose. In various embodiments cellulosomes comprise catalytic subunits such as glycoside hydrolases, polysaccharide lyases and carboxyl esterases bound together by scaffoldins consisting of cohesins connected to other functional units such as the enzymes and carbohydrate binding modules via dockerins.

The terms "percent identity," "% identity," "percent identical," and "% identical" are used interchangeably herein to refer to the percent amino acid sequence identity that is obtained using standard alignment algorithms. For example, the percent sequence identity can be obtained by optimally aligning two sequences, counting the number of identical matches in the alignment and dividing such number of identical matches by the length of the reference sequence.

In various embodiments two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art (see, e.g., Dayhoff et al. (1978), "A model of evolutionary change in proteins"; "Atlas of Protein Sequence and Structure,"Vol. 5, Suppl. 3 (Ed. M. O. Dayhoff), pp. 345-352, Natl. Biomed. Res. Round., Washington, D.C.; and Henikoff et al. (1992) *Proc. Natl. Acad. Sci. USA,* 89: 10915-10919, both of which are incorporated herein by reference). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm, e.g., gapped BLAST 2.0, described in Altschul et al. (1997) *Nucleic Acids Res.,* 25: 3389-3402, and made available to the public at the National Center for Biotechnology Information Website. Optimal alignments, including multiple alignments can be prepared using readily available programs such as PSI-BLAST, which is described by Altschul et al. (1997) *Nucleic Acids Res.,* 25: 3389-3402. In certain embodiments preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOSUM62.

One skilled in the art may also use the ALIGN program incorporating the non-linear algorithm of Myers and Miller (1988) *Comput. Appl. Biosci.* 4: 11-17). For amino acid sequence comparison using the ALIGN program illustrative parameters include a PAM 120 weight residue table, a gap length penalty of 12, and a gap penalty of 4.

The length of polypeptide sequences compared for homology will generally be at least about 16 amino acid residues, usually at least about 20 residues, more usually at least about 24 residues, typically at least about 28 residues, preferably more than about 35 residues, and typically the full length of the mature protein. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences. Pearson, *Methods Enzymol.* 183:63-98 (1990) (herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

Amino acid residues are said to "correspond to each other" or to be "corresponding amino acids" when they occupy the same position in optimally aligned sequences and/or when they occupy the same position in the three dimensional conformation of the subject molecule(s), and/or occupy the same position in a local alignment of conserved domains (the entire sequence may not align, but local domains often do.

An amino acid "position" is denoted by a number that sequentially identifies each amino acid in the reference sequence based on its position relative to the N-terminus. Owing to deletions, insertions, truncations, fusions, and the like that must be taken into account when determining an optimal alignment. The amino acid residue number in a test sequence determined by simply counting from the N-terminal may not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence. The identity of residues in a "test" (variant) sequence corresponding to particular residues in a "parent" sequence can be determined by alignment (e.g., of the entire protein or particular domains) and/or inspection of protein conformation, and/or particular chemistries at designated positions.

An "expression vector" refers to a nucleic acid construct comprising a nucleic acid sequence (e.g., DNA sequence) that is operably linked to a suitable control sequence capable of effecting the expression of the nucleic acid in a suitable host. Such control sequences may include a promoter to effect transcription, an optional operator sequence to control transcription, a sequence encoding suitable ribosome-binding sites on the mRNA, and sequences that control termination of transcription and translation. Different cell types are typically used with different expression vectors. For example, an illustrative promoter for vectors used in *Bacillus* spp. is the AprE promoter; an illustrative promoter used in *E. coli* is the Lac promoter, an illustrative promoter used in *Saccharomyces* spp. is PGK1, an illustrative promoter used in *Aspergillus* spp. glaA, and an illustrative promoter for *Trichoderma* spp. is cbhI. In certain embodiments the vector may be a plasmid, a phage particle, or simply a potential genomic insert. Once transformed into a suitable host, the vector may replicate and function independently of the host genome, or may, under suitable conditions, integrate into the genome itself. In the present specification, plasmid and vector are sometimes used interchangeably. However, the invention is intended to include other forms of expression vectors that serve equivalent functions and which are, or become, known in the art. Thus, a wide variety of host/expression vector combinations may be employed in expressing the nucleic acid sequences described herein. Useful expression vectors, for example, may consist of segments of chromosomal, non-chromosomal and synthetic DNA sequences such as various known derivatives of SV40 and known bacterial plasmids, e.g., plasmids from *E. coli* including col E1, pCR1, pBR322, pMb9, pUC 19 and their derivatives, wider host range plasmids, e.g., RP4, phage DNAs e.g., the numerous derivatives of phage lamda, e.g., NM989, and other DNA phages, e.g., M13 and filamentous single stranded DNA phages, yeast plasmids such as the 2 mu plasmid or derivatives thereof, vectors useful in eukaryotic cells, such as vectors useful in animal cells and vectors derived from combinations of plasmids and phage DNAs, such as plasmids which have been modified to employ phage DNA or other expression control sequences. Expression techniques using the expression vectors of the present invention are known in the art and are described generally in, for example, Sambrook.

"Host strain" or "host cell" means a suitable host for expressing nucleic acids comprising an expression vector as described herein. Illustrative host cells include prokaryotic or eukaryotic hosts, including any transformable microorganism in which expression can be achieved. Certain typical host strains include, but are not limited to, *Bacillus subtilis, Escherichia coli, Trichoderma reesei, Saccharomyces cerevisiae, Aspergillus niger*, and the like.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from its native environment.

The term "polypeptide fragment" as used herein refers to a polypeptide that has a deletion, e.g., an amino-terminal and/or carboxy-terminal deletion and/or internal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long. In certain embodiments the polypeptide fragment is at least 100, or at least 200, or at least 300, or at least 400, or at least 440, or at least 450, or at least 500 amino acid in length. In certain embodiments the fragment comprises or substantially comprises the catalytic domain of an enzyme described herein.

When "homologous" is used in reference to proteins or peptides, it is recognized that residue positions that are not identical often differ by conservative amino acid substitutions. A conservative amino acid substation is typically one that will not substantially change the functional properties of the protein. In various embodiments a "conservative amino acid substitution" is one in which an amino acid residue is substituted by another amino acid residue having a side chain (R group) with similar chemical properties (e.g., charge or hydrophobicity). In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson (1994) *Meth. Mol. Biol.* 24: 307-331 and 25:365-389).

The following six illustrative groups each contain amino acids that are often conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W). These "conservative" substitutions are illustrative and not limiting. Other conservative substitutions are known. In addition numerous methods are available for the prediction of conservative substitutions. For example, SIFT (Sorting Intolerant From Tolerant) is a program that predicts whether an amino acid substitution affects protein function. SIFT has been demonstrated to distinguish between functionally neutral and deleterious amino acid changes in mutagenesis studies and on human polymorphisms (see, e.g., Ng and Henikoff (2001) *Genome Res.*, 11: 863-875 and Ng and Henikoff (2003) *Nucl. Acids Res.*, 31(13): 3812-3814). SIFT is available at http://blocks.fhcrc.org/sift/SIFT.html. Other illustrative methods of identifying conservative mutations (or non-conservative mutations) include, but are not limited to PolyPhen (see, e.g., Stitziel et al. (2004) *Nucleic Acids Res.* 32: D520-522; Stitziel et al. (2003) *J. Mol. Biol.* 327:1021-1030; and "http://www.bork.emblheidelberg.de/PolyPhen"), SNPs3D (see, e.g., Yue et al. (2005) *J. Mol. Biol.* 353:459-473; Yue and Moult (2005) *J. Mol. Biol.* 356:1263-1274; and "http://www.snps3d.org/"), PANTHER PSEC (see, e.g., Thomas et al. (2003) *Genome Res.* 13: 2129-2141; and "https://panther.appliedbiosystems.com/methods/csnp-ScoreForm.jsp"), PMUT (see, e.g., Ferrer-Costa et al. (2005) *Bioinformatics,* 21: 3176-3178; Ferrer-Costa et al. (2002) *J. Mol. Biol.* 315: 771-786; Ferrer-Costa et al. (2004) *Proteins* 57:811-819; and "http://mmb2.pcb.ub.es:8080/PMut"), TopoSNP (see, e.g., Stitziel et al. (2003) supra; Stitziel et al. (2004) supra.; and "http://gila.bioengr.uic.edu/snp/toposnp"), and the like. A review is provided by Ng and Henikoff (2006) *Annu. Rev. Human Genet.* 7: 61-80.

The term "purified" does not require absolute purity; rather, it is intended as a relative term. Thus, for example, a purified product preparation, is one in which the product is more concentrated than the product is in its environment within a cell. For example, a purified wax is one that is substantially separated from cellular components (nucleic acids, lipids, carbohydrates, and other peptides) that can accompany it. In another example, a purified wax preparation is one in which the wax is substantially free from contaminants, such as those that might be present following fermentation.

A "recombinant" nucleic acid molecule or protein is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or proteins, such as genetic engineering techniques. Recombinant is also used to describe nucleic acid molecules that have been artificially manipulated, but contain the same regulatory sequences and coding regions that are found in the organism from which the nucleic acid was isolated.

The standard amino acid abbreviations shown below in Table 1 are used herein.

TABLE 1

Amino acid abbreviations.

| Abbreviation | 1 letter abbreviation | Amino acid name |
|---|---|---|
| Ala | A | Alanine |
| Arg | R | Arginine |
| Asn | N | Asparagine |
| Asp | D | Aspartic acid |
| Cys | C | Cysteine |
| Gln | Q | Glutamine |
| Glu | E | Glutamic acid |
| Gly | G | Glycine |
| His | H | Histidine |
| Ile | I | Isoleucine |
| Leu | L | Leucine |
| Lys | K | Lysine |
| Met | M | Methionine |
| Phe | F | Phenylalanine |
| Pro | P | Proline |
| Pyl | O | Pyrrolysine |
| Ser | S | Serine |
| Sec | U | Selenocysteine |
| Thr | T | Threonine |
| Trp | W | Tryptophan |
| Tyr | Y | Tyrosine |
| Val | V | Valine |
| Asx | B | Aspartic acid or Asparagine |
| Glx | Z | Gultamic acid or Glutamine |
| Xaa | X | Any amino acid |
| Xle | J | Leucine or Isoleucine |

When a Markush Group or a list of particular compounds is described in the specification and/or claims it is intended that in various additional or alternative embodiments any subset of that Markush group or list is contemplated. Thus, for example, a Markush group or list consisting of elements A, B, and C also comprises a disclosure of a Markush Group or list consisting of A, and B, a Markush Group or list consisting of B, and C, and a Markush Group or list consisting of A and C as well as elements A, B, and C individually. Similarly, when elements in one list or Markush group are described as being in combination with elements in another list or Markush group the combination of any one element of one group with any one element of another group is contemplated. Thus where a list or Markush Group consisting of A, B and C is disclosed in combination with another list or Markush Group consisting of D, E, and F, the description is to be recognized as contemplating the combinations A/D, A/E, A/F, B/D, B/E, B/F, C/D, C/E, C/F and/or any combination of A, B, or C with any subgroup or member of D, E, and F, and/or any combination of D, E, or F, with any subgroup or member of A, B, and C.

BRIEF DESCRIPTION OF THE DRAWINGS

FIG. 1A shows the amino acid sequence of the novel *Thermobifida fusca* Cel9A variant (designated "F1", SEQ ID NO:1). FIG. 1B shows the DNA sequence of F1 (SEQ ID NO:2). The sequence shown is a synthetic DNA sequence that has been codon optimized for expression in *E. coli*. With the exception of the novel changes at positions F64, A226, and E246, this DNA sequence encodes the wild-type *Thermobifida fusca* Cel9A amino acid sequence, however, the nucleotide sequence is dissimilar from wild-type *Thermobifida fusca* Cel9A DNA. Note that nucleic acid sequences and amino acid position numbering are for the mature enzyme. They exclude the signal peptide, e.g., MSVTEPPPRRRG RHSRARRFLTSLGATAALTAGMLGVPLATGTAHA (SEQ ID NO:3), although it will be recognized that in certain embodiments, protein(s) comprising the variant cellulolytic peptides described herein attached to a signal peptide are contemplated.

FIG. 4 shows an alignment between wild-type *Thermobifida fusca* Cel9A (SEQ ID NO:4) and *Clostridium phytofermentans* Cphy3367 (SEQ ID NO:5).

FIG. 5 shows structures of wild-type *Thermobifida fusca* Cel9A and *Clostridium phytofermentans* Cphy3367 illustrating 3D similarity. It is believed that the novel F1 variants if transferred, singly or in combination, to homologous positions in Cphy3367 will confer increased activity. Cel9A and Cphy3367 share 66% similarity. At homologous positions, two of the F1 variant positions are identical in Cphy3367 (A226, E246) and the third F1 variant (I64) shares close similarity to wild-type amino acid found in the homologous position in Cphy3367 (L).

FIG. 6 shows additional examples of novel variants cellulolytic peptides exhibiting increased cellulolytic activity (as compared to wild-type). The peptides are designated G03 (SEQ ID NO:6) and G11 (SEQ ID NO:7).

DETAILED DESCRIPTION

Figure 2:
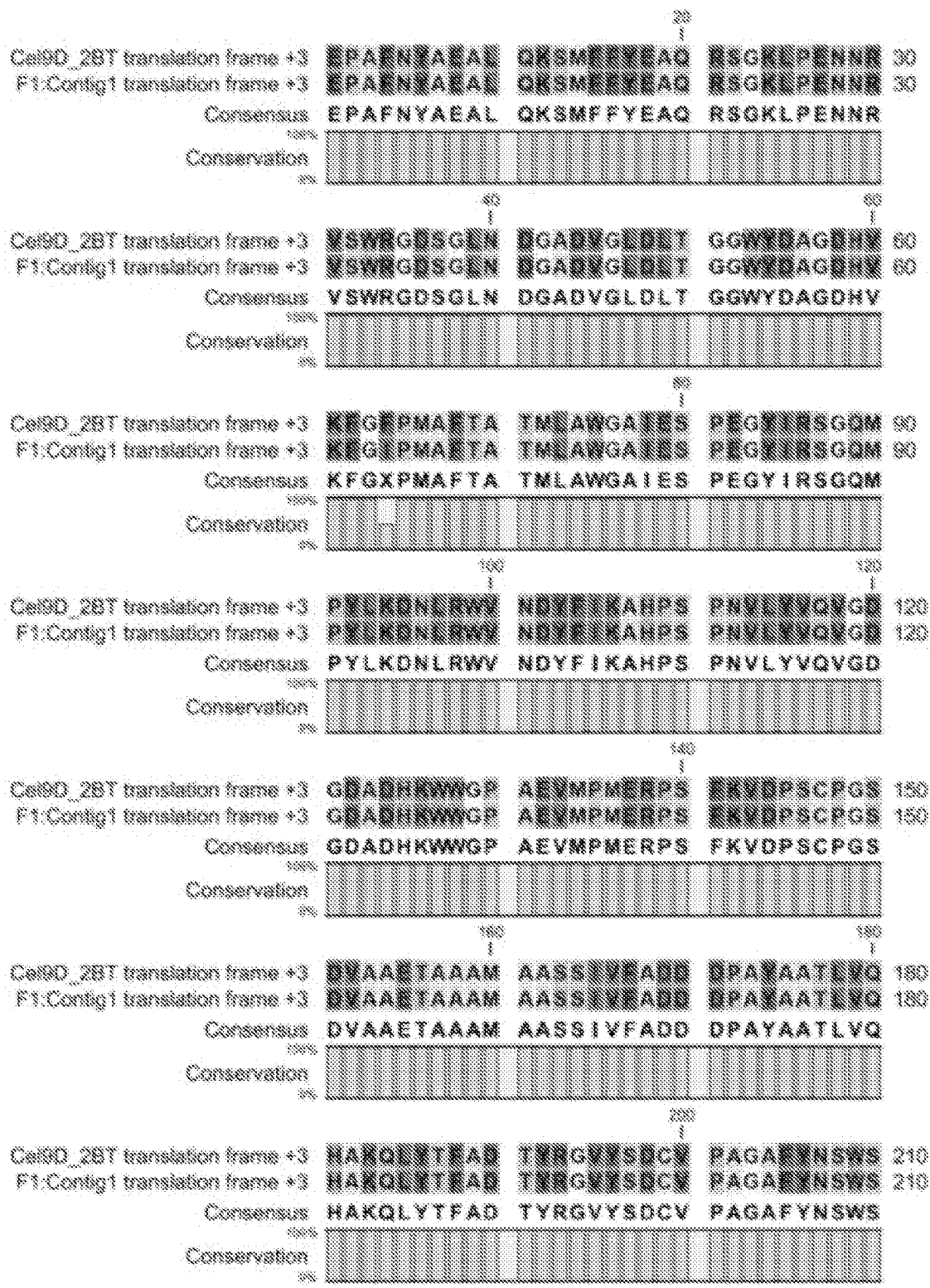
FIG. 2 shows an alignment of wild-type *Thermobifida fusca* Cel9A (SEQ ID NO:4) and F1 (SEQ ID NO:1) amino acid sequences. As shown herein, F1 contains the following amino acid changes: F64I, A226V, and E246G.

In various embodiments novel variant cellulolytic enzymes (cellulases) having improved cellulolytic activity and/or stability are provided herein as well as methods of use of such enzymes. The variant enzymes provided herein have widespread utility in biomass conversion into renewable chemical and biofuel production, textile processing, waste water treatment, animal feed treatment, paper and pulp processing, detergent formulation and the like.

In addition to the enzymes themselves, in certain embodiments, nucleic acids encoding the enzymes, vectors incorporating the nucleic acids, and host cells that express the enzymes are provided.

In certain embodiments the enzymes are displayed on the surface of a cell (e.g., a bacterial cell, a phage, a yeast cell) or on the surface of a particle or component of a bioreactor. In certain embodiments the enzymes are provided as a component of a cellulosome or minicellulosome (e.g., displayed on a bacteria such as *Clostridium*, on a yeast, and the like).

Cellulases are known in the art as enzymes that hydrolyze cellulose (beta-1,4-glucan or beta D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH") and beta-glucosidases (EC 3.2.1.21) ("BG") (see, e.g., Knowles et al. (1987) *TibTech*, 5: 255-261).

It is believed that endoglucanase-type cellulases hydrolyze internal beta-1,4-glucosidic bonds in regions of low crystallinity of the cellulose and exo-cellobiohydrolase-type cellulases hydrolyze cellobiose from the reducing or non-reducing end of cellulose. It follows that the action of endoglucanase components can greatly facilitate the action of exo-cellobiohydrolases by creating new chain ends which are recognized by exo-cellobiohydrolase components. Further, beta-glucosidase-type cellulases have been shown to catalyze the hydrolysis of alkyl and/or aryl β-D-glucosides such as methyl β-D-glucoside and p-nitrophenyl glucoside as well as glycosides containing only carbohydrate residues, such as cellobiose. This yields glucose as the sole product for the microorganism and reduces or eliminates cellobiose which inhibits cellobiohydrolases and endoglucanases.

Cellulases also find a number of uses in detergent compositions including to enhance cleaning ability, as a softening agent and to improve the feel of cotton fabrics (Hemmpel (1991) *ITB Dyeing/Printing/Finishing* 3: 5-14; Tyndall (1992) *Textile Chemist and Colorist* 24: 23-26; Kumar et al. (1997) *Textile Chemist and Colorist,* 29: 37-42). Without being bound to a particular theory, softening and color restoration properties of cellulase have been attributed to the endoglucanase components in cellulase compositions, as exemplified by U.S. Pat. Nos. 5,648,263, 5,691,178, and 5,776,757, which disclose that detergent compositions containing a cellulase composition enriched in a specified endoglucanase component impart color restoration and improved softening to treated garments as compared to cellulase compositions not enriched in such a component.

Cellulase compositions have also been shown to degrade cotton-containing fabrics, resulting in reduced strength loss in the fabric (U.S. Pat. No. 4,822,516), contributing to reluctance to use cellulase compositions in commercial detergent applications. Cellulase compositions comprising endoglucanase components have been suggested to exhibit reduced strength loss for cotton-containing fabrics as compared to compositions comprising a complete cellulase system.

Cellulases have also been shown to be useful in degradation of cellulase biomass to ethanol (wherein the cellulase degrades cellulose to glucose and yeast or other microbes further ferment the glucose into ethanol), in the treatment of mechanical pulp (Pere et al. (1996) *In Proc. Tappi Pulping Conf., Nashville, Tenn.,* 27-31, pp. 693-696), for use as a feed additive (WO 1991/004673) and in grain wet milling.

Variant Enzymes.

In certain embodiments a prototypic variant enzyme is provided designated F1. This enzyme is a variant of *Thermobifida fusca* Cel9A. The amino acid sequence is shown in FIG. 1 and a nucleic acid sequence (codon optimized for expression in *E. coli*) is shown in FIG. 2. The reference/"parent" *Thermobifida fusca* Cel9A wild-type sequence (SEQ ID NO:4) is described in U.S. Pat. No. 7,314,974 (which is incorporated here by reference for the sequences described therein), and is listed also as database entry EMBL-Bank CDS AAB42155. Cel9A is also known as CelD, E-4, E4, Cel9D, and YP_290232. It was a surprising discovery that alterations of one or more residues corresponding to positions F64, A226, and E246 result in an enzyme with greater activity and/or stability.

In view of the conserved nature of glycoside hydrolases, and the highly conserved nature of family 9 glycoside hydrolases, and the very highly conserved nature of theme B family 9 glycoside hydrolases, it is believed that variation of residues in other glycoside hydrolases at one or more positions corresponding to s F64, A226, and/or E246 in *Thermobifida fusca* Cel9A will produce cellulolytic enzymes having increase activity and/or stability.

Thus, for example, without being bound to a particular theory, in view of the strong alignment between wild-type *Thermobifida fusca* Cel9A and *Clostridium phytofermentans* Cphy3367 (see, FIG. 4) and structures showing 3D similarity (see, FIG. 5), it is believed that variants if transferred, singly or in combination, to homologous positions in Cphy3367 will confer increased activity. In this regard, it is noted that Cel9A and Cphy3367 share 66% similarity. At homologous positions, two of the F1 variant positions are identical in Cphy3367 (A226, E246) and the third F1 variant (164) shares close similarity to wild-type amino acid found in the homologous position in Cphy3367 (L).

Thus, in certain embodiments variant cellulotyic enzymes comprising a glycoside hydrolase with or comprising a substitution at one or more positions corresponding to one or more of residues F64, A226, and/or E246 in *Thermobifida fusca* Cel9A are contemplated. Variant cellulolytic enzymes, as contemplated herein, do not include any wild-type and/or naturally occurring enzymes. In certain embodiments the enzyme has at least 50%, or at least 60%, or at least 65%, or at least 70%, or at least 75%, or at least 80%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99% sequence identity with F1, and/or Cel9A, and/or Cphy3367, and/or G03, and/or G11. In certain embodiments the sequence identity is over a region of at least 30 contiguous amino acids, or at least 50 contiguous amino acids, or at least 100 contiguous amino acids, or at least 150 contiguous amino acids, or at least 200 contiguous amino acids, or at least 250 contiguous amino acids, or at least 300 contiguous amino acids, or at least 350 contiguous amino acids, or at least 400 contiguous amino acids, or at least 450 contiguous amino acids, or at least 500 contiguous amino acids, or at least 550 contiguous amino acids, or at least 600 contiguous amino acids, or over the full length of the enzyme(s).

In various embodiments the enzyme comprises no more than 5 additional variations (substitutions, and/or insertions, and/or deletions) at positions other than those corresponding to F64, A226, and/or E246 in *Thermobifida fusca* Cel9A. In various embodiments the variant is a variant of a family 9 glycoside hydrolase. In various embodiments the variant is a variant of a theme B subfamily of said family 9 glycoside hydrolase.

In certain embodiments the variant comprises a substitution at a position corresponding to F64 in *Thermobifida fusca* Cel9A. In various embodiments the variant comprises a substitution at a position corresponding to A226 in *Thermobifida fusca* Cel9A. In certain embodiments the variant comprises a substitution at a position corresponding to E246 in *Thermobifida fusca* Cel9A. In certain embodiments the variant comprises a substitution at positions corresponding to F64 and A226 in *Thermobifida fusca* Cel9A. In certain embodiments the variant comprises a substitution at positions corresponding to F64 and E246 in *Thermobifida fusca* Cel9A. In certain embodiments the variant comprises a substitution at positions corresponding to A226 and E246 in *Thermobifida fusca* Cel9A. In certain embodiments the variant comprises a substitution at positions corresponding to F64, A226, and E246 in *Thermobifida fusca* Cel9A.

In certain embodiments the substitution at a position corresponding position F64 in *Thermobifida fusca* Cel9A is a substitution to I, V, L, or M. In certain embodiments the substitution at a position corresponding position F64 in *Thermobifida fusca* Cel9A is a substitution to I. In certain embodiments the substitution at a position corresponding position A226 in *Thermobifida fusca* Cel9A is a substitution to V, I, L, M, or T. In certain embodiments the substitution at a position corresponding position A226 in *Thermobifida fusca* Cel9A is a substitution to V, I, L, or M. In certain embodiments the substitution at a position corresponding position A226 in *Thermobifida fusca* Cel9A is a substitution to V. In certain embodiments the substitution at a position corresponding position E246 in *Thermobifida fusca* Cel9A is a substitution to G, A, N, or S. In certain embodiments the substitution at a position corresponding position E246 in *Thermobifida fusca* Cel9A is a substitution to G.

In various embodiments the enzyme is a variant of a glycoside hydrolase from an organism selected from the group consisting of archaea, bacteria, and eukaryota. In certain embodiments the enzyme is a variant of a glycoside hydrolase from a gram negative bacterium. In certain embodiments the enzyme is a variant of a glycoside hydrolase from a gram positive bacterium. In certain embodiments the enzyme is a variant of glycoside hydrolase from a bacterial family selected from the group consisting of Thermofidia, Micromonospora, Cellulomonas, Listeria, Pseudomonas, Ruminococcus, Saccharophagus, Streptomyces, Vibrio, Xanthomonas, and Clostridium.

In certain embodiments the variant comprises or consists of a variant of *Thermobifida fusca* Cel9A and/or *Clostridium phytofermentans* Cphy3367. In certain embodiments the variant comprises or consists of *Thermobifida fusca* Cel9A having an amino acid substitution at F64, and/or A226, and/or E246. In certain embodiments the variant comprises or consists of *Thermobifida fusca* Cel9A having an amino acid substitution of F64 to I, V, L, or M, and/or of A226 to V, I, L, M, A, or T, and/or of E246 to G, A, N, or S. In certain embodiments the variant comprises or consists of *Thermobifida fusca* Cel9A having an amino acid substitution of F64I, and/or of A226V, and/or E246G. In certain embodiments the variant comprises or consists of *Thermobifida fusca* Cel9A having an amino acid substitution of F64I, A226V, and E246G.

In certain embodiments the variant comprises or consists of the amino acid sequence of F1, G03, or G11.

In certain embodiments variant enzymes comprising conservative substitutions in any of the variant enzymes described above are contemplated. In various embodiments the variant comprises no more than 1, or 2, or 3, or 4, or 5, or 6, or 7, or 8, or 9, or 10, or 11, or 12, or 13, or 14, or 15, or 16, or 17, or 18, or 19, or 20 conservative substitutions.

In certain embodiments isolated polypeptides comprising a fragment of the above-described amino acid sequences are provided. In various embodiments these fragments preferably include at least 20 contiguous amino acids, more preferably at least 25, 30, 35, 40, 45, 50, 60, 70, 80, 90, 100, 150, 200, 250, 300, 350, or even more contiguous amino acids. In certain embodiments the fragments comprise particular domains of the peptide(s) and/or possess a particular activity (e.g., carbohydrate binding, hydrolase activity, etc.). In certain embodiments peptides comprising, consisting essentially of, or consisting of the catalytic domain of the variant cellulolytic enzyme are provided. In this context "consisting essentially of" refers to a protein variant or fragment thereof that preserves the catalytic activity of the full-length variant peptide.

In certain embodiments, fusions between the above-described polypeptide sequences and heterologous polypeptides are provided. The heterologous sequences can, for example, include sequences designed to facilitate purification, e.g. histidine tags, and/or visualization of recombinantly-expressed proteins. Other non-limiting examples of protein fusions include those that permit display of the encoded protein on the surface of a phage or a cell, fusions to intrinsically fluorescent proteins, such as green fluorescent protein (GFP), fusion to signal peptides to direct polypeptide processing and export, fusion to cellulose binding module(s), fusion to dockerin domain(s), fusion to cohesion domain(s), fusion to fibronectin-like domain(s), fusions to the IgG Fc region, and the like. The fusions can be direct or can be by way of intervening peptide linker regions/domains.

Preparation of Host Cell Transformants and Expression of Variant Enzymes.

In various embodiments polynucleotide fragments encoding one or more variant enzymes described herein and, optionally other polypeptides (e.g., other enzymes) may be incorporated into heterologous nucleic acid constructs or vectors, capable of introduction into, and replication in a host cell (e.g., a filamentous fungal or yeast cell, a bacterial cell, etc.). Generally any vector may be used as long as it is replicable and viable in the cells into which it is introduced. Large numbers of suitable vectors and promoters are known to those of skill in the art, and are commercially available. Cloning and expression vectors are also described in Sambrook et al., 1989, Ausubel F M et al., 1989, and Strathern et al., The Molecular Biology of the Yeast *Saccharomyces*, 1981, each of which is expressly incorporated by reference herein.

Vectors.

In various embodiments nucleic acids encoding one or more of the variant cellulolytic enzymes (cellulases) described herein are inserted into vectors suitable for expressing the enzyme(s) in a host cell. In such vector(s), the nucleic acid encoding the enzyme(s) is operably linked to one or more promoters and/or other regulatory sequences.

The term "operably linked" refers herein to a configuration in which a control sequence is appropriately placed at a position relative to the coding sequence of the DNA sequence such that the control sequence influences the expression of a polypeptide. When used herein, the term "coding sequence" is intended to cover a nucleotide sequence that directly specifies the amino acid sequence of its protein product. The boundaries of the coding sequence are generally determined by an open reading frame that usually begins with the ATG start codon. The coding sequence typically includes a DNA, cDNA, and/or recombinant nucleotide sequence.

As used herein, the term "expression" includes any step involved in the production of the polypeptide including, but not limited to, transcription, post-transcriptional modification, translation, post-translational modification, and secretion.

The term "expression vector" refers herein to a DNA molecule, linear or circular, that comprises a segment encoding a polypeptide of the invention, and which is operably linked to additional segments that provide for its transcription.

In certain embodiments nucleic acid constructs comprise a vector, such as, a plasmid, a cosmid, a phage, a virus, a bacterial artificial chromosome (BAC), a yeast artificial chromosome (YAC), and the like, into which a nucleic acid sequence(s) of the variant enzyme(s) have been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

Polynucleotides encoding the variant enzyme(s) described herein can be incorporated into any of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that transduces and/or expresses genetic material into a cell, and, if replication is desired, which is replicable and viable in the relevant host can be used.

When incorporated into an expression vector, the nucleic acid sequence(s) encoding the desired enzyme(s) are operatively linked to an appropriate transcription control sequence (promoter) to direct mRNA synthesis, e.g., T5 promoter. Examples of such transcription control sequences particularly suited for use in transgenic plants include the cauliflower mosaic virus (CaMV) and figwort mosaic virus (FMV). Other promoters known to control expression of genes in prokaryotic or eukaryotic cells or their viruses and which can be used in some embodiments include SV40 promoter, *E. coli* lac or trp promoter, phage lambda $P_L$ promoter, tac promoter, T7 promoter, and the like. Examples of suitable promoters useful for directing the transcription of the nucleotide constructs in a filamentous fungal host cell include promoters such as cbh1, cbh2, egl1, egl2, pepA, hfb1, hfb2, xyn1, amy, and glaA (see, e.g., Nunberg et al. (1984) *Mol. Cell Biol.*, 4: 2306-2315; Boel et al. (1984) *EMBO J.* 3: 1581-1585)). In bacterial host cells, suitable promoters include the promoters obtained from the *E. coli* lac operon, *Streptomyces coelicolor* agarase gene (dagA), a gene from a *Bacillus* sp., such as, for example, the *Bacillus subtilis* levansucranse gene (sacB), the *Bacillus licheniformis* alpha-amylase gene (amyl), the *Bacillus megaterium* InhA gene, the *Bacillus stearothermophilus* maltogenic amylase gene (amyM), the *Bacillus amyloliquefaciens* alpha-amylase gene (amyQ), *Bacillus subtilis* xylA and xylB genes, the xylose promoter (Pxyl) from *Bacillus megaterium*, the promoter obtained from the prokaryotic beta-lactamase gene, and so forth.

In various embodiments an expression vector optionally contains a ribosome binding site for translation initiation, and a transcription terminator, such as PinII. The vector also optionally includes appropriate sequences for amplifying expression, e.g., an enhancer.

In various embodiments the vector or DNA construct may also generally include a signal peptide coding region that codes for an amino acid sequence linked to the amino terminus of a polypeptide and which directs the encoded polypeptide into the cell's secretory pathway. Suitable signal peptides include, but are not limited to the *Bacillus megaterium* penicillin G acylase signal peptide sequence.

Other illustrative signal peptide coding regions for bacterial host cells may be obtained from the genes of *Bacillus* NCIB 11837 maltogenic amylase, *B. stearothermophilus* alpha-amylase, *B. licheniformis* subtilisin, *B. licheniformis* beta-lactamase, *B. stearothermophilus* neutral proteases (nprT, nprS, nprM) and *B. subtilis* prsS. Further illustrative signal sequences are described in Simonen and Palva (1993), Microbiological Reviews 57: 109-137. Effective signal peptide coding regions for filamentous fungal host cells include but are not limited to the signal peptide coding regions obtained from *Aspergillus oryzae* TAKA amylase, *Aspergillus niger* neutral amylase, *Aspergillus niger* glucoamylase, *Rhizomucor miehei* asparatic proteinase, *Humicola insolens* cellulase and *Humicola lanuginosa* lipase. Variants of these signal peptides and other signal peptides are suitable, as well as expression mutants thereof having one or more silent mutations.

In various embodiments the expression vectors optionally contain one or more selectable marker genes to provide a phenotypic trait for selection of transformed host cells. Suitable marker genes include those coding for antibiotic resistance such as, ampicillin, kanamycin, chloramphenicol, or tetracycline resistance. Further examples include the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance. Additional selectable marker genes include dihydrofolate reductase or neomycin resistance for eukaryotic cell culture, and tetracycline or ampicillin resistance in *E. coli*.

The vector may further contain genetic elements that facilitate integration by either homologous or non-homologous recombination. Genetic elements that facilitate integration by homologous recombination have sequence homology to targeted integration sites in the genomic sequence of the desired expression host cell. Genetic elements or techniques which facilitate integration by non-homologous recombination include restriction enzyme-mediated integration (REMI) (see Manivasakam et al. (1998) *Mol. Cell Biol.* 18(3): 1736-1745), transposon-mediated integration, and other elements and methods that are well known in the art.

In certain embodiments the cellulase polynucleotides described herein can also be fused, for example, in-frame to nucleic acids encoding a secretion/localization sequence, to target polypeptide expression to a desired cellular compartment, membrane, or organelle of a cell, or to direct polypeptide secretion to the periplasmic space, to the cell membrane or cell wall, or into the cell culture media. Such sequences are known to those of skill, and include secretion leader peptides, organelle targeting sequences (e.g., nuclear localization sequences, endoplasmic reticulum (ER) retention signals, mitochondrial transit sequences, peroxisomal transit sequences, and chloroplast transit sequences), membrane localization/anchor sequences (e.g., stop transfer sequences, GPI anchor sequences), and the like.

An illustrative expression vector for the expression of variant cellulases described herein is detailed in Example 1, hereinbelow. Vectors as described herein can be employed to transform an appropriate host to permit the host to express one or more variant cellulolytic enzymes described herein.

Host Cell Transformants (Expression Hosts)

In certain embodiments, host cells host cells transformed with nucleic acid molecules or vectors encoding one or more of the cellulolytic enzymes described herein. In some embodiments, these cells carry the nucleic acid sequences on vectors, which may, but need not, be freely replicating vectors. In other embodiments, the nucleic acids have been integrated into the genome of the host cells.

Suitable host cells include, but are not limited to bacterial cells, algal cells, plant cells, fungal cells, insect cells and mammalian cells. In one illustrative embodiment suitable host cells include *E coli* (e.g., SHuffle™ competent *E. coli* available from New England BioLabs in Ipswich, Mass.). As used herein, genetically modified or recombinant host cell includes the progeny of host cell(s) that comprise a polynucleotide that encodes a variant enzyme described herein.

In some embodiments, the genetically modified or recombinant host cell is a eukaryotic cell. Suitable eukaryotic host cells include, but are not limited to, fungal cells, algal cells, insect cells, and plant cells. Suitable fungal host cells include, but are not limited to, Ascomycota, Basidiomycota, Deuteromycota, Zygomycota, Fungi imperfecti. Certain preferred fungal host cells include yeast cells and filamentous fungal cells. Suitable filamentous fungi host cells include, for example, any filamentous forms of the subdivision Eumycotina and Oomycota. (see, e.g., Hawksworth et al., In Ainsworth and Bisby's Dictionary of The Fungi, 8.sup.th edition, 1995, CAB International, University Press, Cambridge, UK, which is incorporated herein by reference). Filamentous fungi are characterized by a vegetative mycelium with a cell wall composed of chitin, cellulose and other complex polysaccharides. The filamentous fungi host cells are morphologically distinct from yeast.

In certain illustrative, but non-limiting embodiments the filamentous fungal host cell may be a cell of a species of, but not limited to *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella*, or teleomorphs, or anamorphs, and synonyms or taxonomic equivalents thereof.

In some embodiments the filamentous fungal host cell is of the *Trichoderma* species, e.g., *T. longibrachiatum, T. viride* (e.g., ATCC 32098 and 32086), *Hypocrea jecorina* or *T. reesei, T. koningii*, and *T. harzianum*, and the like.

In some embodiments of the invention, the filamentous fungal host cell is of the *Aspergillus* species, e.g., *A. awamori, A. funigatus, A. japonicus, A. nidulans, A. niger, A. aculeatus, A. foetidus, A. oryzae, A. sojae*, and *A. kawachi*.

In some embodiments the filamentous fungal host cell is of the *Chrysosporium* species, e.g., *C. lucknowense, C. keratinophilum, C. tropicum, C. merdarium, C. inops, C. pannicola*, and *C. zonatum*.

In some embodiments of the invention, the filamentous fungal host cell is of the *Fusarium* species, e.g., *F. bactridioides, F. cerealis, F. crookwellense, F. culmorum, F. graminearum, F. graminum, F. oxysporum, F. roseum*, and *F. venenatum*. In some embodiments of the invention, the filamentous fungal host cell is of the *Neurospora* species, (e.g., *N. crassa*), the *Humicola* species, (e.g., *H. insolens, H. grisea*, and *H. lanuginose*) the *Mucor* species (e.g., *M. miehei* and *M. circinelloides*) the *Rhizopus* species (e.g., *R. oryzae* and R. *niveus*) the *Trichoderma* species (e.g., *T. reesei*), the *Trametes* species (e.g., *T. villosa* and *T. versicolor*), and the like.

In certain embodiments enzyme(s) described herein are expressed in a yeast host. Suitable yeast host cells include, but are not limited to *Candida, Hansenula, Saccharomyces, Schizosaccharomyces, Pichia, Kluyveromyces*, and *Yarrowia*. In some embodiments the yeast cell is *Hansenula polymorpha, Saccharomyces cerevisiae, Saccharomyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans*, or *Yarrowia lipolytica*.

In certain embodiments the host cell is an algal such as, *Chlamydomonas* (e.g., *C. Reinhardtii*) and *Phormidium* (*P.* sp. ATCC29409).

In other embodiments, the host cell is a prokaryotic cell. Suitable prokaryotic cells include gram positive, gram negative and gram-variable bacterial cells. The host cell may be a species of, but not limited to *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacte-*

*rium, Geobacillus, Haemophilus, Helicobacter, Klebsiella, Lactobacillus, Lactococcus, Ilyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmus, Streptomyces, Streptococcus, Synecoccus, Saccharomonospora, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia* and *Zymomonas.*

In some embodiments the bacterial host strain is an industrial strain. Numerous bacterial industrial strains are known and suitable in the methods and compositions described herein.

In some embodiments the bacterial host cell is of the *Agrobacterium* species (e.g., *A. radiobacter, A. rhizogenes, A. rubi*), the *Arthrobacter* species (e.g., *A. aurescens, A. citreus, A. globformis, A. hydrocarboglutamicus, A. mysorens, A. nicotianae, A. paraffineus, A. protophonniae, A. roseoparaffinus, A. sulfureus, A. ureafaciens*), the *Bacillus* species (e.g., *B. thuringiensis, B. anthracis, B. megaterium, B. subtilis, B. lentus, B. circulars, B. pumilus, B. lautus, B. coagulans, B. brevis, B. firmus, B. alkaophius, B. licheniformis, B. clausii, B. stearothermophilus, B. halodurans* and *B. amyloliquefaciens.* In particular embodiments, the host cell will be an industrial *Bacillus* strain including but not limited to *B. subtilis, B. pumilus, B. licheniformis, B. megaterium, B. clausii, B. stearothermophilus* and *B. amyloliquefaciens* some preferred embodiments of a *Bacillus* host cell include *B. subtilis, B. licheniformis, B. megaterium, B. stearothermophilus* and *B. amyloliquefaciens*), the *Clostridium* species (e.g., *C. acetobutylicum, C. tetani* E88, *C. lituseburense, C. saccharobutylicum, C. perfringens, C. beijerinckii*), the *Corynebacterium* species (e.g., *C. glutamicum, C. acetoacidophilum*) the *Escherichia* species (e.g., *E. coli*), the *Erwinia* species (e.g., *E. uredovora, E. carotovora, E. ananas, E. herbicola, E. punctata, E. terreus*), the *Pantoea* species (e.g., *P. citrea, P. agglomerans*), the *Pseudomonas* species, (e.g., *P. putida, P. aeruginosa, P. mevalonii*), the *Streptococcus* species (e.g., *S. equisimiles, S. pyogenes, S. uberis*), the *Streptomyces* species (e.g., *S. ambofaciens, S. achromogenes, S. avermitilis, S. coelicolor, S. aureofaciens, S. aureus, S. fungicidicus, S. griseus, S. lividans*), the *Zymomonas* species (e.g., *Z. mobilis, Z. lipolytica*), and the like.

In various embodiments strains that may be used in the practice of the invention including both prokaryotic and eukaryotic strains, are readily accessible to the public from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Introduction of the Nucleic Acid Encoding a Variant Cellulase into a Host Cell

Introduction of a vector or DNA construct into a host cell can be effected by any of a number of methods known to those of skill in the art. Illustrative methods include, but are not limited to calcium phosphate transfection, DEAE-Dextran mediated transfection, electroporation, or other common techniques (see, e.g., Davis et al. (1986) Basic Methods in Molecular Biology).

The engineered host cells can be cultured in conventional nutrient media modified as appropriate for activating promoters, selecting transformants, and/or amplifying the cellulase polynucleotide. Culture conditions, such as temperature, pH and the like, are those typically used with the host cell selected for expression, and will be apparent to those skilled in the art (see, e.g., Sambrook, Ausubel and Berger, as well as, for example, Freshney (1994) Culture of Animal Cells, a Manual of Basic Technique, third edition, Wiley-Liss, New York; Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York) and Atlas and Parks (eds) The Handbook of Microbiological Media (1993) CRC Press, Boca Raton, Fla.).

The methods of transformation may result in the stable integration of all or part of the transformation vector into the genome of the host cell. However, transformation resulting in the maintenance of a self-replicating extra-chromosomal transformation vector is also contemplated.

Production and Recovery of Cellulase Variants

In certain embodiments methods of making the variant enzymes described herein are provided. The methods comprising providing a host cell transformed with a nucleic acid construct encoding one or more of the enzymes described herein; culturing the transformed host cell in a culture medium under conditions that cause the polynucleotide to express the encoded variant enzyme(s); and optionally recovering or isolating the expressed variant enzyme, or recovering or isolating the culture medium containing the expressed enzyme variant(s), or recovering or isolating cells displaying the expressed enzyme variant(s). In certain embodiments the methods further provides optionally lysing the transformed host cells after expressing the encoded variant enzyme(s) and optionally recovering or isolating the expressed variant enzyme(s) from the cell lysate.

Typically, recovery or isolation of the variant enzyme(s) is from the host cell culture medium, the host cell or both, using protein recovery techniques that are well known in the art, including those described herein.

Following transformation of a suitable host strain and growth (cultivating or culturing) of the host strain to an appropriate cell density, the selected promoter may be induced by appropriate means (e.g., temperature shift or chemical induction) and cells are cultured for an additional period. Cells are typically harvested by centrifugation, disrupted by physical or chemical means, and the resulting crude extract may be retained for further purification. Microbial cells employed in expression of proteins can be disrupted by any convenient method, including freeze-thaw cycling, sonication, mechanical disruption, or use of cell lysing agents, or other methods, which are well known to those skilled in the art.

Many references are available for the culture and production of many cells, including cells of bacterial, plant, animal (especially mammalian) and archebacterial origin. See e.g., Sambrook, Ausubel, and Berger (all supra), as well as Freshney (1994) Culture of Animal Cells, a Manual of Basic Technique, third edition, Wiley-Liss, New York and the references cited therein; Doyle and Griffiths (1997) Mammalian Cell Culture: Essential Techniques John Wiley and Sons, NY; Humason (1979) Animal Tissue Techniques, fourth edition W.H. Freeman and Company; and Ricciardelli, et al., (1989) In vitro Cell Dev. Biol. 25:1016-1024, all of which are incorporated herein by reference. For plant cell culture and regeneration, Payne et al. (1992) Plant Cell and Tissue Culture in Liquid Systems John Wiley & Sons, Inc. New York, N.Y.; Gamborg and Phillips (eds) (1995) Plant Cell, —Tissue and Organ Culture; Fundamental Methods Springer Lab Manual, Springer-Verlag (Berlin Heidelberg New York); Jones, ed. (1984) Plant Gene Transfer and Expression Protocols, Humana Press, Totowa, N.J. and Plant Molecular Biology (1993) R. R. D. Croy, Ed. Bios Scientific Publishers, Oxford, U.K. ISBN 0 12 198370 6, all of which are incorporated herein by reference. Cell culture media in general are set forth in Atlas and Parks (eds.) The Handbook of Microbiological Media (1993) CRC Press, Boca Raton, Fla., which is incorporated herein by reference. Additional information for cell culture is found in available commercial literature such as the Life Science Research Cell Culture Catalogue (1998) from Sigma-Aldrich, Inc (St Louis, Mo.) ("Sigma-LSRCCC") and, for example, The Plant Culture Catalogue and supplement (1997) also from Sigma-Aldrich, Inc (St Louis, Mo.) ("Sigma-PCCS"), all of which are incorporated herein by reference.

In some embodiments, cells expressing the variant enzyme(s) described herein are grown under batch or continuous fermentations conditions. Classical batch fermentation is a closed system, wherein the compositions of the medium is set at the beginning of the fermentation and is not subject to artificial alternations during the fermentation. A variation of the batch system is a fed-batch fermentation which also finds use in the present methods described herein. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

The resulting variant enzyme(s) can be recovered/isolated and optionally purified by any of a number of methods known in the art. For example, the polypeptide may be isolated from the nutrient medium by conventional procedures including, but not limited to, centrifugation, filtration, extraction, spray-drying, evaporation, chromatography (e.g., ion exchange, affinity, hydrophobic, chromatofocusing, and size exclusion), or precipitation. Protein refolding steps can be used, as desired, in completing the configuration of the mature protein. Finally, high performance liquid chromatography (HPLC) can be employed in the final purification steps. In addition to the references noted supra, a variety of purification methods are well known in the art, including, for example, those set forth in Sandana (1997) *Bioseparation of Proteins*, Academic Press, Inc.; Bollag et al. (1996) Protein Methods, 2.sup.nd Edition, Wiley-Liss, NY; Walker (1996) The Protein Protocols Handbook Humana Press, NJ; Harris and Angal (1990) Protein Purification Applications: A Practical Approach, IRL Press at Oxford, Oxford, England; Harris and Angal Protein Purification Methods: A Practical Approach, IRL Press at Oxford, Oxford, England; Scopes (1993) Protein Purification: Principles and Practice 3.sup.rd Edition, Springer Verlag, NY; Janson and Ryden (1998) Protein Purification: Principles, High Resolution Methods and Applications, Second Edition, Wiley-VCH, NY; and Walker (1998) Protein Protocols on CD-ROM, Humana Press, NJ In certain embodiments cell-free transcription/translation systems can also be employed to produce the variant enzyme(s) described herein. Several such systems are commercially available. A general guide to in vitro transcription and translation protocols is found in Tymms (1995) *In vitro Transcription and Translation Protocols: Methods in Molecular Biology*, Volume 37, Garland Publishing, NY, which is incorporated herein by reference.

Enzymes and Enzyme Systems Displayed on Surfaces.

In certain embodiments the variant enzymes described herein or enzyme complexes comprising the variant enzymes are displayed on the surfaces of substrates, particles, and/or microorganisms.

Substrates, Microparticles, and Nanoparticles.

In certain embodiments the variant enzymes described herein are displayed a surface. Illustrative surfaces induce, for example, the surface of a particle, microbead or particle (both termed "microparticles" for ease of discussion), nanoparticle, a planar substrate (e.g., a microarray substrate), a wall, channel or chamber in a fluidics or microfluidics device, a surface of a cell culture vessel, and a surface comprising a bioreactor, and the like.

Such surfaces may comprise any of a number of materials including, but not limited to a ceramic, a plastic, a glass, a metal, a mineral, and the like. Illustrative materials include, but are not limited to cellulose and cellulose variants (methylcellulose, hydroxyethyl cellulose, etc.), sepharose, polystyrene, polymethylacrylate, polypropylene, latex, polytetrafluoroethylene, polyacrylonitrile, polycarbonate, silica, quartz, metals, metal oxides or nitrides, semiconductors, nanorods, quantum dots, and the like. In various embodiments the materials and may be fluorescent and/or magnetic and/or paramagnetic.

Microorganism Display Systems.

In various embodiments the variant enzyme(s) described herein can be displayed on the surface of a microorganism (e.g., a yeast or other fungus, a bacterium, a phage etc.). The expression and display/presentation of heterologous proteins on the surface of microorganisms is well known to those of skill in the art. Typically in "cell-based" display systems the polypeptides (e.g., variant enzyme(s) to be displayed are inserted into or replace all or part of a gene encoding a cellular protein that is expressed on the cell surface (package surface protein).

Numerous cell-based surface display platforms are well known in the art. These include, for example, prokaryotic cells such as *E. coli, S. typhimurium, P. aeruginosa, B. subtilis, P. aeruginosa, V. cholerae, K pneumonia, N. gonorrhocae, N. meningitides*, and the like. They also include eukaryotic cells such as yeast cells, filamentous fungal cells, and the like.

As an illustration of prokaryotic based surface display, Wu et al. (2006) *FEMS Microbiol. Lett.* 256: 119-25 describe cell surface display of Chi92 on *Escherichia coli* using ice nucleation protein. Cho et al. (2002) *Appl. Environ. Microbiol.* 68: 2026-2030 describe cell surface display of organophosphorus hydrolase in *E. coli*, Lee et al. (2005) *Appl Environ Microbiol.* 71: 8581-8586 reported cell surface display of lipase in *Pseudomonas putida* KT2442 using OprF as an anchoring motif, Shimazu et al. (2003) *Biotechnol Prog.* 19:1612-1614 describe cell surface display of a protein (organophosphorus hydrolase) in *Pseudomonas putida* using an ice-nucleation protein anchor. In addition, Desvaux et al. (2006) *FEMS Microbiol Lett.* 256: 1-15 reviews cell surface display of proteins in Gram-positive bacteria in general.

Examples of yeast display systems include, but are not limited to for example, *Saccharomyces cerevisiae, Schizosaccharomyces pombe, Hanseula*, or *Pichia pastoris*. Other display systems include, but are not limited to phage display, insect display, and mammalian cell display systems.

The foregoing display systems are intended to be illustrative and no limiting. Using the teachings provided herein numerous other methods and systems for displaying the variant enzyme(s) described herein on the surface of microorganisms will be available to one of skill in the art.

Cellulosomes and Minicellulosomes

The digestion of cellulose and hemicellulose can be facilitated by the use of several types of enzymes acting cooperatively. Often, at least three categories of enzymes are utilized to convert cellulose into fermentable sugars: endoglucanases that cut the cellulose chains at random; cellobiohydrolases that cleave cellobiosyl units from the cellulose chain ends and beta-glucosidases that convert cellobiose and soluble cellodextrins into glucose. Among these three categories of enzymes involved in the biodegradation of cellulose, cellobiohydrolases are useful for the degradation of native crystalline cellulose. Cellobiohydrolase I, also referred to as a cellulose 1,4-beta-cellobiosidase or an exoglucanase, exo-cellobiohydrolase or 1,4-beta-cellobiohydrolase catalyzes the hydrolysis of 1,4-beta-D-glucosidic linkages in cellulose and cellotetraose, by the release of cellobiose from the non-reducing ends of the chains. Cellobiohydrolase II activity is identical, except that cellobiohydrolase II attacks from the reducing ends of the chains.

In various embodiments the cellulolytic enzymes (including one or more of the variant enzymes described herein) are organized into a cellulosome or minicellulosome. Cellulosomes are complexes of cellulolytic enzymes natively created by bacteria such as *Clostridium* and *Bacteroides*. They consist of catalytic subunits such as glycoside hydrolases, polysaccharide lyases and carboxyl esterases typically bound together by scaffoldins consisting of cohesins connected to other functional units such as the enzymes and carbohydrate binding modules typically via dockerins. They assist in digestion or degradation of plant cell wall materials, most notably cellulose. Artificial cellulosomes (e.g., minicellulsomes) can be engineered into and expressed in a variety of organisms, including, but not limited to certain bacteria, (e.g., *Clostridia*, *Bacteroides*), yeasts, and fungi.

The displayed cellulosomes can be simple cellulosome systems containing a single scaffoldin, or complex cellulosome systems exhibit multiple types of interacting scaffoldins. In various embodiments each scaffoldin can contain one, two, three, four, five, six, seven, eight, nine, or 10 or more cohesin domains. The arrangement of the modules on the scaffoldin subunit and the specificity of the cohesin(s) and/or dockerin for their modular counterpart determine the overall architecture of the cellulosome. Several different types of scaffoldins have been described: the primary scaffoldins incorporate the various dockerin-bearing subunits directly into the cellulosome complex, adaptor scaffoldins increase the repertoire or number of components into the complex, and the anchoring scaffoldins attach the complex to the bacterial cell surface.

In certain embodiments the cellulolytic enzymes comprising the cellulosome or individually displayed on the surface of a microorganism include one or more variant enzymes described herein and, optionally, one or more additional enzymes collected from the group consisting of an exoglucanase, an endoglucanase, a glycosyl hydrolase, a cellulase, a hemicellulase, a xylanase, a cellobiohydrolase, a β-glucosidase, a mannanse, a xylosidase (e.g., a β-xylosidase), an arabinofuranosidase, and/or a glucose oxidase.

Methods of designing and expressing cellulosomes and minicellulosomes are well known to those of skill in the art.

Thus, for example, Mingardon et al. (2007) *Applied and Environmental Microbiology*, 73(12): 3822-3832 describe the assembly of minicellulosomes on *Saccharomyces*. Tsai et al. (2010) *Appl Environ Microbiol*. 76(22):7514-7520 describing the expression of minicellulosomes using a synthetic yeast consortium comprising four different engineered yeast strains capable of either displaying a trifunctional scaffoldin, Scaf-ctf (SC), carrying three divergent cohesin domains from *Clostridium thermocellum* (t), *Clostridium cellulolyticum* (c), and *Ruminococcus flavefaciens* (f), or secreting one of the three corresponding dockerin-tagged cellulases (endoglucanase [AT], exoglucanase [EC/CB], or β-glucosidase [BF]). Mingardon et al. (2005) Appl Environ Microbiol. 71(3):1215-1222 describe heterologous production, assembly, and secretion of a minicellulosome by *Clostridium acetobutylicum*. Hyeon et al. (2010) FEMS Microbiol Lett 310(1): 39-47 describe engineering *Saccharomyces cerevisiae* for assembly of minicellulosomes by heterologous expression of a recombinant scaffolding protein from *Clostridium cellulovorans* and a chimeric endoglucanase E from *Clostridium thermocellum*. The chimeric endoglucanase E fused with the dockerin domain of endoglucanase B from *C. cellulovorans* was assembled with the recombinant scaffolding protein.

Due to the production of highly versatile cellulosomes and the anaerobic, thermophilic, ethanologenic nature, of *C. thermocellum*, it, and other thermophilic microorganisms are good cellulosome expression systems for consolidated bioprocessing (CBP). CBP features the production of cellulases and hemicellulases, hydrolysis of cellulose and hemicellulose, and, fermentation of hydrolysis products, all in one step. Using a thermophilic strain such as *C. thermocellum* means less time for cooling and easy removal of ethanol at higher temperatures. It also means no addition of oxygen during the biorefining process and fermentation of glucose to produce ethanol and organic acids (see, e.g. Demain et al. (2005) *Microbiol Mole Biol Rev.*, 69(1): 124-154).

It will be recognized that the cellulosome systems identified above are intended to be illustrative and not limiting. Using the teachings provided herein, numerous cellulosomes comprising one or more of the variant enzymes described herein and expression systems the display of such cellulosomes will be available to one of skill in the art.

Uses of the Variant Cellulolytic Enzymes.

The variant cellulolytic enzymes and the nucleic acid constructs encoding such enzymes find utility in a wide variety of applications some of which are described below.

In certain embodiments the variant cellulolytic enzymes described herein find utility in detergent compositions that exhibit enhanced cleaning ability, function as a softening agent and/or improve the feel of cotton fabrics (e.g., "stone washing" or "biopolishing"), in compositions for degrading wood pulp into sugars (e.g., for bio-ethanol production), and/or in feed compositions.

For example, the rate of hydrolysis of cellulosic products may be increased by using a transformant expressing one or more copies of the enzymes having greater cellulolytic activity described herein. This permits degradation of products that contain cellulose or heteroglycans at a faster rate and to a greater extent. Products made from cellulose such as paper, cotton, cellulosic diapers and the like can be degraded more efficiently in a landfill. Thus, the product obtainable from the transformants or the transformants alone may be used in compositions to help degrade by liquefaction a variety of cellulose products that add to the overcrowded landfills.

Separate saccharification and fermentation is a process whereby cellulose present in biomass, e.g., corn stover, is converted to glucose and subsequently yeast strains convert glucose into ethanol. Simultaneous saccharification and fermentation is a process whereby cellulose present in biomass, e.g., corn stover, is converted to glucose and, at the same time and in the same reactor, yeast strains convert glucose into ethanol. Thus, in another approach, the variant cellulase enzymes described herein find utility in the degradation of biomass to ethanol. Ethanol production from readily available sources of cellulose provides a stable, renewable fuel source.

Cellulose-based feedstocks are comprised of agricultural wastes, grasses and woods and other low-value biomass such as municipal waste (e.g., recycled paper, yard clippings, etc.). Ethanol may be produced from the fermentation of any of these cellulosic feedstocks. However, the cellulose must first be converted to sugars before there can be conversion to ethanol.

A large variety of feedstocks may be used with the cellulolytic enzyme variants described herein, and the one selected for use may depend on the region where the conversion is being done. For example, in the Midwestern United States agricultural wastes such as wheat straw, corn stover and bagasse may predominate while in California rice straw may predominate. However, it should be understood that any available cellulosic biomass may be used in any region.

In certain embodiments a cellulase composition containing one or more variant cellulases described herein finds utility in ethanol production. Ethanol from this process can be further used as an octane enhancer or directly as a fuel in lieu of gasoline which is advantageous because ethanol as a fuel source is more environmentally friendly than petroleum derived products. It is believed that the use of ethanol will improve air quality and possibly reduce local ozone levels and smog. Moreover, utilization of ethanol in lieu of gasoline can be of strategic importance in buffering the impact of sudden shifts in non-renewable energy and petrochemical supplies.

In various embodiments ethanol can be produced via saccharification and fermentation processes from cellulosic biomass such as trees, herbaceous plants, municipal solid waste and agricultural and forestry residues. However, the ratio of individual cellulase enzymes within a naturally occurring cellulase mixture produced by a microbe may not be the most efficient for rapid conversion of cellulose in biomass to glucose. It is known that endoglucanases act to produce new cellulose chain ends which themselves are substrates for the action of cellobiohydrolases and thereby improve the efficiency of hydrolysis of the entire cellulase system. Therefore, the use of increased or optimized enzymes as described herein can greatly enhance the production of ethanol.

Thus, the enzyme variants described herein find use in the hydrolysis of cellulose to its sugar components. In one embodiment, a variant enzyme is added to the biomass prior to the addition of a fermentative organism. In a second embodiment, a variant enzyme is added to the biomass at the same time as a fermentative organism. Optionally, there may be other cellulase components present in either embodiment.

In certain embodiments the variant cellulase is displayed on a particle (or other surface), or on a microorganism (e.g., on a yeast or other fungus, or bacteria).

In certain embodiments the variant cellulase is provided as a component of a cellulosome or minicellulosome displayed on a particle or a microorganism (e.g., on a yeast or other fungus, or bacteria).

Where the enzyme(s), cellulosome, and/or minicellulosome is presented on a microorganism, the microorganism can be dormant or inactive and in which case the enzyme, cellulosome, and/or minicellulosome simply acts as an enzyme or enzyme complex facilitating the degradation of cellulosic materials to produce sugars.

In certain embodiments the microorganism is active and the enzyme, cellulosome, and/or minicellulosome is displayed and contacted to the cellulosic material in a culture system (e.g., in a consolidated bioreactor).

In another embodiment the cellulosic feedstock can be pretreated. Pretreatment may be by elevated temperature and the addition of either of dilute acid, concentrated acid or dilute alkali solution. In certain embodiments the pretreatment solution can be added for a time sufficient to at least partially hydrolyze the hemicellulose components and then neutralized.

In a typical biomass conversion process, enzymatic saccharification can produce sugars that are made available for biological or chemical conversions to other intermediates or end-products. Therefore, the sugars generated from biomass find use in a variety of processes in addition to the generation of ethanol. Non-limiting examples of such conversions are fermentation of glucose to ethanol, and other biological conversions of glucose to 2,5-diketo-D-gluconate (see, e.g. U.S. Pat. No. 6,599,722), lactic acid, succinate, 1,3-propanediol, 2,3-butanediol, the chemical and biological conversions of xylose to xylitol (see, e.g., WO 1998/021339), and the like.

In various embodiments detergent compositions employ besides the variant cellulase(s) described herein, a surfactant, including anionic, non-ionic and ampholytic surfactants, optionally a hydrolase, building agents, bleaching agents, bluing agents and fluorescent dyes, caking inhibitors, solubilizers, cationic surfactants and the like.

In various embodiments the cellulase(s) described herein can be added to the detergent composition either in a liquid diluent, in granules, in emulsions, in gels, in pastes, and the like. Such forms are well known to the skilled artisan. When a solid detergent composition is employed, the cellulase composition is preferably formulated as granules. Preferably, the granules can be formulated so as to contain a cellulase protecting agent (see, e.g., U.S. Pat. No. 6,162,782).

In various illustrative, but non-limiting embodiments the cellulase compositions can be are employed from about 0.00005 weight percent to about 5 weight percent relative to the total detergent composition. More typically the cellulase compositions are employed from about 0.0002 weight percent to about 2 weight percent relative to the total detergent composition.

These uses are intended to be illustrative and non-limiting. Using the teachings provided herein other uses of the variant cellulases described herein will be available to one of skill in the art.

EXAMPLES

The following examples are offered to illustrate, but not to limit the claimed invention.

Example 1

Expressing and Testing Activity of Cellulase Variants

Generating Plasmid

DNA encoding novel variants was PCR amplified using LIC-tailed gene-specific primers as follows: 0.3 µM primers (forward 5'-TAC TTC CAA TCC AAT GCA ATG GAA CCG GCA TTC AAC TAC-3' (SEQ ID NO:8); reverse 5'-TTA TCC ACT TCC AAT GTT ATT ATG CCA GAG CGC ACG-3' (SEQ ID NO:9), 1 ng template DNA, 1×KOD Hot Start Master Mix (#71842-3, EMD Chemicals), water to 50 µL.

Reactions were incubated at 95° C. for 2 min to activate the polymerase followed by 30× thermal cycling at 95° C. for 20 s, 60° C. for 10 s, and 70° C. for 30 s. Resulting amplicons were band-purified by agarose gel electrophoresis to remove non-specific amplicons and purified by using the illustra GFX PCR DNA and Gel Band Purification kit (#28-9034-71, GE Healthcare) according to manufacture protocols. 0.2 pmol of purified amplicon was treated at 22° C. for 30 min and 75° C. for 20 min with 1 U of LIC-qualified T4 DNA polymerase (#70099-3, EMD Chemicals) in a 20 µL reaction containing 2.5 mM dCTP, 5.0 mM DTT, and 1×T4 DNA polymerase buffer to generate sticky overhangs. 0.02 pmol of the treated product was hybridized with 0.014 pmol of similarly prepared LIC vector in a 3.4 µL reaction at 25° C. for 5 min followed by the addition of 1 µL 25 mM EDTA and another 25° C. 5 min incubation.

Transforming *E. coli*

The hybridization reaction above was transformed into SHuffle™ competent *E. coli* (#C3029H, New England Biolabs) as follows: 4.4 µL of hybridized insert and vector were added to thawed SHuffle™ cells and incubated on ice for 30 min. The mixture was heat shocked at 42° C. for 30 s followed by a 1 hr outgrowth at 30° C. in 250 µL SOC media. The mixture was split and plated onto 2 pre-warmed LB plates containing 100 µg/mL carbenicillin and grown inverted for 16 hr at 37° C.

Generating Cellulase

Individual colonies were picked into 1 mL Magic Media (#K6803, Life Technologies) and incubated at 37° C. for 6 hrs followed by 25° C. for 18 hrs, both with shaking at 900 rpm. OD600 measurements were made on 50 µL of sample to determine cell growth. Cell pellets were recovered by decanting the supernatant after centrifuging at 3,000 rpm at 4° C. for 10 min. Cell pellets were lysed for 20 min in 200 µL BugBuster™ (#71456-3, EMD Chemicals) stock solution (40 mL BugBuster™, 400 µL 100 mM PMSF, 40 µL 1 mg/mL pepstatin, 40 µL 1 mg/mL leupeptin, 40 mg lysozyme). Lysed cells were centrifuged at 3,000 rpm at 4° C. for 30 min and the cleared lysate supernatant containing expressed cellulase variant was recovered for testing.

Determining Activity of Generated Cellulases

Figure 3:
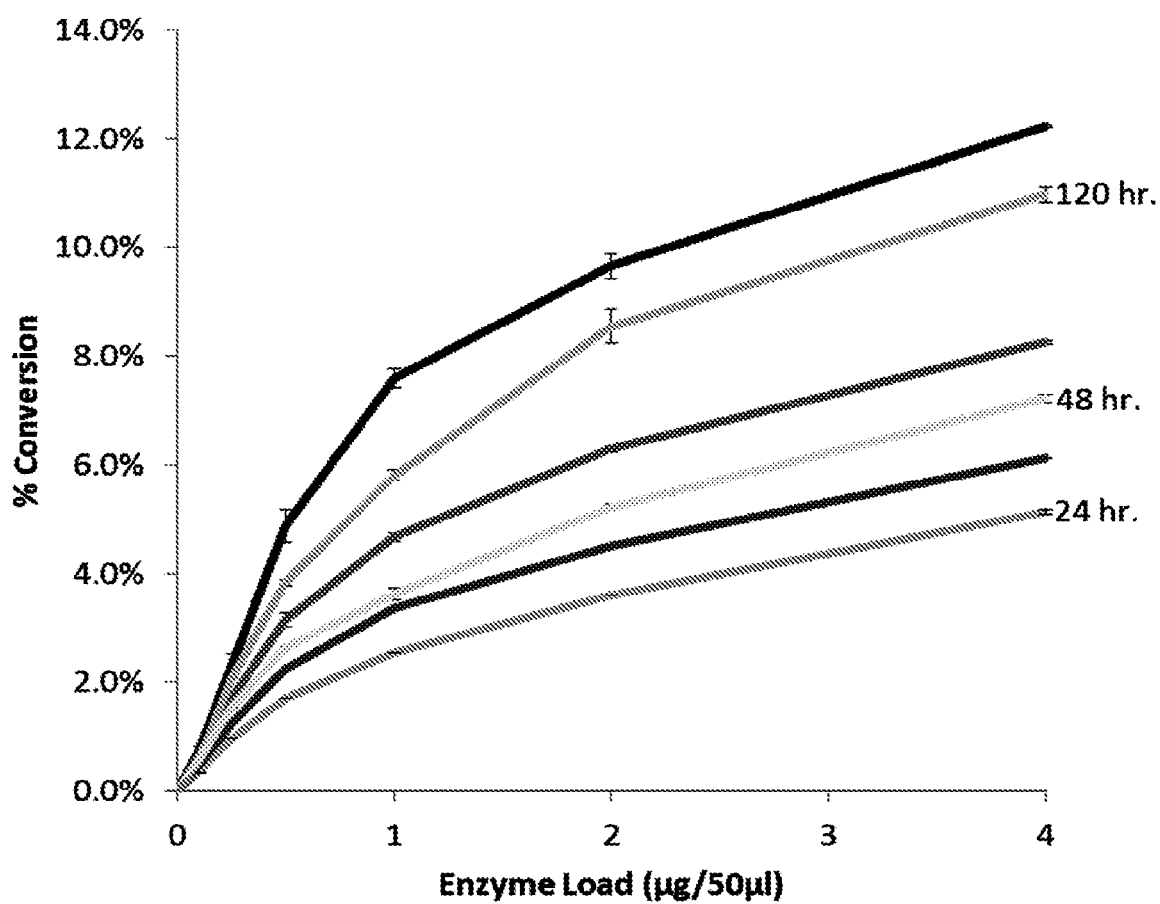
FIG. 3 shows data illustrating the improved activity of F1 as compared to wild-type. F1 exhibits 20-30% increased specific activity. Activity of wild-type Cel9A and F1 at various enzyme loadings for 24, 48, and 120 hour digestions. Key: F1 activity dark (upper) line, wild-type activity (lower) light line.

5 µL of cleared lysate diluted 1:10 in 50 mM HEPES buffer pH 7.2 was combined with 45 µL of 1.1% carboxymethyl cellulose (CMC) and incubated at 50° C. for 30 min. After incubation, 140 µL of stock p-hydroxy-benzoic-acid-hydrazide (PHBAH) solution (0.179% solution of PHBAH in 0.1M NaOH) was combined with 10 µL of the CMC digestion and incubated at 95° C. for 5 min. Absorbance at 410 nm from a 100 µL sample was measured to determine the amount of liberated reducing sugars by the cellulase variant. Measurements were calibrated to a glucose standard curve and compared to wild-type activity under identical conditions. Improved variant F1 and wild-type Cel9A and were tested at 24, 48, and 120 hours. Results are shown below in FIG. 3.

Example 2

Biofuel Production by Using Enzyme Variant F1

The following procedure may be used to produce ethanol from biomass. Generally, the procedure comprises simultaneous saccharification and fermentation (SSF) of pretreated lignocellulosic biomass whereby cellulases convert the biomass into accessible sugar and yeast ferment the sugar into ethanol.

Biomass may be pretreated in various manners. One method is to solubilize the biomass in concentrated phosphoric acid then precipitate the swollen cellulose using cold water. The cellulose is collected and washed with sufficient water to neutralize the pH. Alternatively, the biomass may be pretreated with dilute sulfuric acid. Briefly, milled and washed biomass at 20% total solids concentration is treated for 3-12 min in 0.5-1.41% (w/w liquid phase) $H_2SO_4$ at 165-183° C. Following treatment, the biomass is washed with water.

Simultaneous saccharification and fermentation is conducted in a shaking incubator (150 rpm) at a working volume of 100 mL in 250-mL baffled flasks. The washed pretreated biomass is loaded to a level of 6-7% (w/w) cellulose fraction and combined with 35 mg cellulase enzyme variant F1 per gram of cellulose and beta-glucosidase such as ACCELLERASE™ BG (Danisco A/S, Copenhagen, DK) at 0.05 mL product per gram of cellulose. The medium consists of yeast extract (1% [w/v]), peptone (2% [w/v]), and citrate buffer (0.05 M). The initial pH is adjusted to 5.2 using NaOH, and then the culture is inoculated with the yeast, *Saccharomyces cerevisiae* $D_5A$, to achieve an initial optical density (at 600 nm) of 0.5. The flask is maintained at 32-38° C. for 7 days.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A variant cellulolytic enzyme, said variant cellulotyic enzyme comprising a glycoside hydrolase comprising a substitution at one or more positions corresponding to residues F64, A226, and/or E246 of the *Thermobifida fusca* Cel9A sequence of SEQ ID NO: 4.

2. The cellulolytic enzyme of claim 1, said variant cellulotyic enzyme comprising a glycoside hydrolase consisting of a substitution at one or more positions corresponding to residues F64, A226, and/or E246 of the *Thermobifida fusca* Cel9A sequence of SEQ ID NO: 4.

3. The cellulolytic enzyme of claim 1, wherein said enzyme comprises an amino acid sequence having at least 70% sequence identity with the *Thermobifida fusca* Cel9A sequence of SEQ ID NO: 4.

4. The cellulolytic enzyme of claim 1, wherein said enzyme comprises no more than 5 additional variations at positions other than those corresponding to residues F64, A226, and/or E246 of the *Thermobifida fusca* Cel9A sequence of SEQ ID NO: 4.

5. The cellulolytic enzyme according to claim 1, wherein said variant is a variant of a family 9 glycoside hydrolase.

6. The cellulolytic enzyme according to claim 1, wherein said variant is a variant of a theme B subfamily of said family 9 glycoside hydrolase.

7. The cellulolytic enzyme according to claim 1, wherein said variant comprises a substitution at a position corresponding to residue F64 of the *Thermobifida fusca* Cel9A sequence of SEQ ID NO: 4.

8. The cellulolytic enzyme according to claim 1, wherein said variant comprises a substitution at a position corresponding to residue A226 of the *Thermobifida fusca* Cel9A sequence of SEQ ID NO: 4.

9. The cellulolytic enzyme according to claim 1, wherein said variant comprises a substitution at a position corresponding to residue E246 of the *Thermobifida fusca* Cel9A sequence of SEQ ID NO: 4.

10. The cellulolytic enzyme according to claim 1, wherein said variant comprises a substitution at positions corresponding to residues F64 and A226 of the *Thermobifida fusca* Cel9A sequence of SEQ ID NO: 4.

11. The cellulolytic enzyme according to claim 1, wherein said variant comprises a substitution at positions corresponding to residues F64 and E246 of the *Thermobifida fusca* Cel9A sequence of SEQ ID NO: 4.

12. The cellulolytic enzyme according to claim 1, wherein said variant comprises a substitution at positions corresponding to residues A226 and E246 of the *Thermobifida fusca* Cel9A sequence of SEQ ID NO: 4.

13. The cellulolytic enzyme according to claim 1, wherein said variant comprises a substitution at positions corresponding to residues F64, A226, and E246 of the *Thermobifida fusca* Cel9A sequence of SEQ ID NO: 4.

14. The cellulolytic enzyme according to claim 1, wherein said substitution at a position corresponding to residue F64 of the *Thermobifida fusca* Cel9A sequence of SEQ ID NO: 4 is a substitution to I, V, L, or M.

15. The cellulolytic enzyme of claim 14, wherein said substitution at a position corresponding to residue F64 of the *Thermobifida fusca* Cel9A sequence of SEQ ID NO: 4 is a substitution to I.

16. The cellulolytic enzyme according to claim 1, wherein said substitution at a position corresponding to residue A226 of the *Thermobifida fusca* Cel9A sequence of SEQ ID NO: 4 is a substitution to V, I, L, M, or T.

17. The cellulolytic enzyme of claim 16, wherein said substitution at a position corresponding to residue A226 of the *Thermobifida fusca* Cel9A sequence of SEQ ID NO: 4 is a substitution to V, I, L, or M.

18. The cellulolytic enzyme of claim 16, wherein said substitution at a position corresponding to residue A226 of the *Thermobifida fusca* Cel9A sequence of SEQ ID NO: 4 is a substitution to V.

19. The cellulolytic enzyme according to claim 1, wherein said substitution at a position corresponding to residue E246 of the *Thermobifida fusca* Cel9A sequence of SEQ ID NO: 4 is a substitution to G, A, N, or S.

20. The cellulolytic enzyme of claim 19, wherein said substitution at a position corresponding to residue E246 of the *Thermobifida fusca* Cel9A sequence of SEQ ID NO: 4 is a substitution to G.

21. The cellulolytic enzyme according to claim 1, wherein said enzyme is a variant of a glycoside hydrolase from an organism selected from the group consisting of archaea, bacteria, and eukaryota.

22. The cellulolytic enzyme of claim 21, wherein said enzyme is a variant of a glycoside hydrolase from a gram negative bacterium.

23. The cellulolytic enzyme of claim 21, wherein said enzyme is a variant of a glycoside hydrolase from a gram positive bacterium.

24. The cellulolytic enzyme of claim 21, wherein said enzyme is a variant of glycoside hydrolase from a bacterial family selected from the group consisting of Thermofidia, Micromonospora, Cellulomonas, Listeria, Pseudomonas, Ruminococcus, Saccharophagus, Streptomyces, Vibrio, Xanthomonas, and Clostridium.

25. The cellulolytic enzyme of claim 1, wherein said enzyme is a variant of *Thermobifida fusca* Cel9A.

26. The cellulolytic enzyme of claim 1, wherein said enzyme is a variant of *Clostridium phytofermentans* Cphy3367.

27. The cellulolytic enzyme according to claim 1, wherein said enzyme is attached to or operably linked to a signal peptide.

28. The cellulolytic enzyme according to claim 1, wherein said cellulolytic enzyme is present and/or displayed on the surface of an organism selected from the group consisting of a phage, a fungus, an alga, and a bacterium.

29. The cellulolytic enzyme according to claim 1, wherein said cellulolytic enzyme is present and/or displayed on a substrate or the surface of a particle.

30. The cellulolytic enzyme of claim 29, wherein said substrate or particle comprises a material selected from the group consisting of a plastic, a glass, a mineral, a synthetic polymer, a biological polymer, and a metal.

31. The cellulolytic of claim 30, wherein said substrate or particle comprises a biological polymer selected from the group consisting of a carbohydrate, a protein, a nucleic acid, and a polysaccharide.

32. The cellulolytic enzyme of claim 29, wherein said substrate or particle comprises a surface of a microfluidic channel or chamber, a surface of a bioreactor, or a surface of a bioreactor.

33. The cellulolytic enzyme according to claim 1, wherein said cellulolytic enzyme is a component of a cellulosome or a minicellulosome.

34. The cellulolytic enzyme of claim 33, wherein said cellulosome is on the surface of a yeast, bacteria, or non-yeast fungus.

35. The cellulolytic enzyme according to claim 33, wherein said cellulosome comprises one or more additional enzymes selected from the group consisting of an endocellulase, an exocellulase, a beta-glucosidase (cellobiase), an oxidative cellulose, a xylanase, a hemicellulase, a lichenase, a chitenase, a xylanase, a cellulose phosphorylase, and a cellulose disrupting protein.

36. A nucleic acid that encodes a cellulolytic enzyme according to claim 1.

37. The nucleic acid of claim 36, wherein said nucleic acid comprises codons optimized for expression in a host cell.

38. The nucleic acid of claim 36, wherein said nucleic acid comprises codons optimized for expression in a host selected from the group consisting of a bacterium, a yeast, a fungus, an alga, an insect, and a mammalian cell.

39. The nucleic acid of claim 36, wherein said nucleic acid comprises codons optimized for expression in *E. coli*.

40. A vector comprising the nucleic acid according to claim 36.

41. A host cell comprising the nucleic acid according to claim 36.

42. The host cell of claim 41, wherein said host cell is selected from the group consisting of an archiobacterium, a bacterium, a yeast cell, a fungal cell, an algal cell, a plant cell, an insect cell, and a mammalian cell.

43. A method of producing a cellulase, said method comprising: a) culturing the host cell according to claim 41 in a suitable culture medium under suitable conditions to produce cellulase; and (b) obtaining the produced cellulase.

44. A method of producing an enzyme variant, comprising introducing a substitution in the amino acid sequence of an endoglucanase at one or more positions corresponding to of residues F64, A226, and/or E246 of the *Thermobifida fusca* Cel9A sequence of SEQ ID NO: 4.

45. A method of degrading cellulosic biomass into fermentable sugars, said method comprising: contacting said cellulosic biomass with a cellulolytic enzyme according to claim 1 under conditions in which said enzyme partially or fully degrades cellulose in said cellulosic biomass to form one or more fermentable sugars.

46. The method of claim 45, wherein said cellulosic biomass comprises one or more materials selected from the group consisting of an agricultural plant waste (e.g., corn stover, cereal straw, sugarcane bagasse), a plant waste from an industrial processes (e.g., sawdust, paper pulp), an a non-food energy crop (e.g., switchgrass).

47. The method of claim 46, wherein said cellulosic biomass comprises one or more materials selected form the group consisting of grasses, rice hulls, bagasse, jute, hemp, flax, bamboo, sisal, abaca, straw, corn cobs, corn stover, alfalfa, hay, coconut hair, seaweed, and algae.

48. A cellulolytic composition comprising a plurality of cellulolytic enzymes at least one of which is an enzyme according to claim 1.

49. The composition of claim 48, wherein said composition comprise a second enzyme selected from the group consisting of an endocellulase, an exocellulase, a beta-glucosidase (cellobiase), an oxidative cellulose, a xylanase, a hemicellulase, a lichenase, a chitenase, a xylanase, and a cellulose phosphorylase.

50. A detergent composition comprising a cellulolytic enzyme according to claim 1, and a surfactant.

51. The detergent composition of claim 50, wherein said detergent comprises a laundry detergent, a dish detergent, or an industrial detergent.

52. The cellulolytic enzyme of claim 1, wherein said enzyme comprises an amino acid sequence having at least 80% sequence identity with the *Thermobifida fusca* Cel9A of SEQ ID NO: 4.

53. The cellulolytic enzyme of claim 1, wherein said enzyme comprises an amino acid sequence having at least 90% sequence identity with the *Thermobifida fusca* Cel9A of SEQ ID NO: 4.

54. The cellulolytic enzyme of claim 1, wherein said enzyme comprises an amino acid sequence having at least 95% sequence identity with the *Thermobifida fusca* Cel9A of SEQ ID NO: 4.

55. The cellulolytic enzyme of claim 1, wherein said enzyme comprises an amino acid sequence having at least 97% sequence identity with the *Thermobifida fusca* Cel9A of SEQ ID NO: 4.

56. The cellulolytic enzyme of claim 1, wherein said enzyme comprises the amino acid sequence of SEQ ID NO: 1.

57. The method of claim 46, wherein said enzyme comprises an amino acid sequence having at least 95% sequence identity with the *Thermobifida fusca* Cel9A of SEQ ID NO: 4.

58. The method of claim 46, wherein said enzyme comprises the amino acid sequence of SEQ ID NO: 1.

* * * * *